US006855867B1

(12) United States Patent
Allen et al.

(10) Patent No.: US 6,855,867 B1
(45) Date of Patent: Feb. 15, 2005

(54) PLANT GLUTAMINE AMIDOTRANSFERASE HOMOLOGS

(76) Inventors: Stephen M. Allen, 2225 Rosewood Dr., Wilmington, DE (US) 19810; Lisa L. Huang, 1423 Old Wilmington Rd., Hockessin, DE (US) 19707; Saverio Carl Falco, 1902 Millers Rd., Arden, DE (US) 19810; J. Antoni Rafalski, 2028 Longcome Dr., Wilmington, DE (US) 19810

( * ) Notice: Subject to any disclaimer, the term of this patent is extended or adjusted under 35 U.S.C. 154(b) by 0 days.

(21) Appl. No.: 09/831,233

(22) PCT Filed: Nov. 4, 1999

(86) PCT No.: PCT/US99/25950

§ 371 (c)(1),
(2), (4) Date: Sep. 14, 2001

(87) PCT Pub. No.: WO00/28053

PCT Pub. Date: May 18, 2000

Related U.S. Application Data

(60) Provisional application No. 60/107,275, filed on Nov. 5, 1998.

(51) Int. Cl.[7] .......................... A01H 1/00; C07H 21/04; C07K 14/415; C12N 5/14; C12N 9/00

(52) U.S. Cl. .......................... 800/295; 435/6; 435/69.1; 435/468; 435/419; 435/252.3; 435/320.1; 530/370; 536/23.6; 800/278

(58) Field of Search .......................... 435/6, 69.1, 468, 435/419, 252.3, 320.1; 530/370; 536/23.2, 23.6; 800/278, 295

(56) References Cited

FOREIGN PATENT DOCUMENTS

| EP | 0 580 161 A1 | 1/1994 |
| WO | 96/40885 A2 | 12/1996 |
| WO | 98/21589 A1 | 5/1998 |

OTHER PUBLICATIONS

Alexandra E. Shedlovsky et al., J. Biol. Chem., vol. 237:3725–3730, 1962, A defect in histidine biosynthesis causing an adenine deficiency.
Alexandra E. Shedlovsky et al., J. Biol. Chem., vol. 237:3731–3736, 1962, The enzymatic basis of an adenine-histidine relationship is *Escherichia coli*.
Richard J. Galloway et al., Journ. of Bacteriol., vol. 144(3):1068–1075, Histidine starvation and adenosine 5'–triphosphate depletion in chemotaxis of *Salmonella typhimurium*.
Jun–ichi Shio et al., Jour. of Biol. Chem., vol. 257(14):7969–7975, 1982, Requirement of ATP in bacterial chemotaxis.

K. Burton, Biochem., J., vol. 61:473–483, 1955, The relation between the synthesis of deoxyribonucleic acid and the synthesis of protein in the multiplication of bacteriophage T2.
K. Burton, Biochem. J., vol. 66:488–489, 1957, A catalytic action of L–histidine in purine biosynthesis.
Jens Stougaard et al., Jour. of Bacteriol., vol. 170(1):250–257, 1988, Regulation of nitrogenase synthesis in histidine auxotrophs of *Klebsiella pneumontae* with altered levels of adenytate nucleotides.
Mark S. Johnson et al., App. & Environ. Microbiol., vol. 59(10):3509–3512, 1993, Comparison of methods for specific depletion of ATP in *Salmonalla typhimurium*.
National Center for Biotechnology Information General Identifier No. 4455213, May 5, 1999, Bevan, M. et al.
National Center for Biotechnology Information General Identifier No. 3219164, Feb. 5, 1999, Fujimori, K. et al., An arabidopsis cDNA encoding a bifunctional glutamine amidotransferase/cyclase suppresses the histidine auxtrophy of a *Saccharomyces cerevisiae* his7 mutant.
Ko Fujimori et al., FEBS Letters, vol. 428:299–234, 1998, An arabidopsis cDNA encoding a bifunctional glutamine amidotransterase/cyclase suppresses the histidine auxotrophy of a *Saccharomyces cerevisias* his7 mutant.
Thomas J. Klem et al., Biochemistry, vol. 32:5177–5186, 1993, Imidazole glycerol phosphate synthase: The glutamine amidotransferase in histidine biosynthesis.
EMBL Sequence Library Database Accession No.: AW066760, Oct. 18, 1999, Walbot, V., Maize ESTs from various cDNA libraries sequenced at Stanford University.
EMBL Sequence Library Database Accession No.: AI899863, Jul. 28, 1999, Shoemaker R., et al., Public Soybean EST Project.
EMBL sequence Library Database Accession No.: CAB36536, Aug. 17, 1999, Devan, M. et al., EU arabidopsis sequencing project.
Kazuhiko Tagawa et al,, Biochem. Biophys. Res. Comm., vol. 177(1):377–387, 1991, Alzhekmer's disease amyloid beta–clipping enzyme (APP secretase): Identification, purification, and characterization of the enzyme.
S. Parvathy et al., Biochemistry, vol. 37: 1680–1685, 1998, Alzhelmer's amyloid precursor protein alpha–secretase is inhibited by hydroxamic acid–based zinc metalloprotease inhibitors: similarities to the angiotensin converting enzyme secretase.

(List continued on next page.)

*Primary Examiner*—Phuong T. Bui
(74) *Attorney, Agent, or Firm*—Morgan & Finnegan, L.L.P.

(57) ABSTRACT

This invention relates to an isolated nucleic acid fragment encoding a histidine biosynthetic enzyme. The invention also relates to the construction of a chimeric gene encoding all or a portion of the histidine biosynthetic enzyme, in sense or antisense orientation, wherein expression of the chimeric gene results in production of altered levels of the histidine biosynthetic enzyme in a transformed host cell.

14 Claims, 4 Drawing Sheets

OTHER PUBLICATIONS

Dido Vassilacopoulou et al., J. of Neurochemistry, vol. 64:2140–2146, 1995, Full–length and truncated Alzheimer amyloid precursors in chromaffin granules: solubillzation of membrane amyloid precursor is mediated by an enzymatic mechanism.

A. Jeannette Potts et al., Exp. Cell Res., vol. 212:2–9, 1994, Proteolytic cleavage of the Integrin beta4 subunit.

Christian Haass et al., Center for Neurological Dis., vol. 12:1291–1296, 1996, The swedish mutation causes early-onset Alzhelmer's disease by beta–secretase cleavage within the secretory pathway.

P.E. Hartman et al., J. Gen. Microbiol., vol. 22:323–353, 1960, Fine structure mapping by complete transduction between histidine–requiring salmonelia mutants.

FIGURE 1A

```
                                                                                               ↓
SEQ ID NO:15   MEATAAPFSSI--VSSRQNFSSSSSIRASSPASLFLSQKSIGNVNRKFKSPRSLSVRASS
SEQ ID NO:02   HEKELAS------TKPQNGFRIRAAl----------------------------------AGA
SEQ ID NO:04   MQPPLQAQGAMANVAAILTVPCSAGRRPKRSNQ-----PRGCGSVSV-------SVSVRASS
SEQ ID NO:08   ------------------------------------------------------------
SEQ ID NO:06   ------------------------------------------------------------
SEQ ID NO:10   MVAA--------------TSINAVPCSAGR-PKRRSQ-----RRG------AS------TVAVRASG
SEQ ID NO:12   ------------------------------------------------------------
SEQ ID NO:14   ------------------------------------------------------------
               1                                                           60

* * ****** *** ****** * *** *** *** ****** ****** ****** *********
SEQ ID NO:15   TSDSVVTLLDYGAGNVRSIRNALRHLGFSIKDVQTPGDILNADRLIFPGVGPFAPAMDVL
SEQ ID NO:02   GGDSVVTLLDYGAGNVRSVRNAIRTLGFDIKDVQKPEDILNAKRLIFPGVGAFAPAMDVL
SEQ ID NO:04   GANTV-TLLDYGAGNVRSVRNAIRYLGFDIRDVQSPEDIVXAEXVVFPGVGAFGSAMDVX
SEQ ID NO:08   ------------------------------------------------------------
SEQ ID NO:06   ------------------------------------------------------------
SEQ ID NO:10   DASTV-TLLDYGAGNVRSVRNAIRHLGFGIRDVRSPEXILAADRLVFPG----------V
SEQ ID NO:12   -----VTLLDYGAGNVRSVRNAIRFLGFDIKDVQTPQDILNASRLVFPGVGAFAAAMEVL
SEQ ID NO:14   ------------------------------------------------------------
               61                                                          120

* * ****** *** ****** *  ****  *   *   ****   ****  * *   *
SEQ ID NO:15   NRTGMAEALCKYIENDRPF  LGI C LGLQLLFD-S  SEQNGPVKGLGVIPGIVGREDASAGIR
SEQ ID NO:02   IRKGLAEALCTYIQNDRPF  LGI C LGLQLLFE-S  SEENGPIQGLGLIPGRVGRFESSNGLR
SEQ ID NO:04   TRTGMXNALREYIQRERPF  XG- I LGLQLLFGFQ  XGXXXRVSGLGVISGVXRRFEXSSNGLI
SEQ ID NO:08   -------YPRGTGPF  LGI C LGLQLLFGFQ  ---------------------------
SEQ ID NO:06   --------------  AF- I ---        ---------------------------
SEQ ID NO:10   ----G---------  --- - ---        ---------------------------
SEQ ID NO:12   --------------  --- - ---        ---------------------------
SEQ ID NO:14   ----SKT-------  --- - ---        ---------------------------
               121                                                         180
```

FIGURE 1B

```
                  ******* **   *       **********  ***********  ** *********  **  **
SEQ ID NO:15      VPHIGWNALQVGKDSEILDDVGNRHVYFVHSYRAIPSDENKDWISSTCNYGESFISSIRR
SEQ ID NO:02      VPHIGWHALDIKEGSAILDDVGNQHVYFVHSYRA-NAEDNKEWISSTCSYGDDFIASIQK
SEQ ID NO:04      ------------------------------------------------------------
SEQ ID NO:08      VPHVGWNALQXTXXXPLLQGADGQXVYFXHSYRVLAS-----------------------
SEQ ID NO:06      ------------------------------------------------------------
SEQ ID NO:10      ------------------------------------------------------------
SEQ ID NO:12      ------------------------------------------------------------
SEQ ID NO:14      ------------------------------------------------------------
                                                                              240
                                                          181

**   *****             *****  *****  *****  *   ***********   **
SEQ ID NO:15      GN  VHAVQF H  E  KSGEVGLSVLRRFLHPKL--PATQKPMEGKASKLAKRVIACLDVRTNDK
SEQ ID NO:02      GN  VHAVQF H  P  E  KSGGVGLSILRRFLNADSFNNKRQKPMNGKASKLAKRVIACLDVRANDN
SEQ ID NO:04      --                                                          --
SEQ ID NO:08      --                                                          --
SEQ ID NO:06      --                                                          --
SEQ ID NO:10      --                                                          --
SEQ ID NO:12      --                                                          --
SEQ ID NO:14      --                                                          --
                  241                                                         300

*****  ***********  *****   *************  ********************  **
SEQ ID NO:15      GDLVVTKGDQYDYDVREQSNENEVRNLGKPVDLAGQYYKDGADEISFLNITGFRDFPLGDLP
SEQ ID NO:02      GDLVVTKGDQYDYDVRERTEENEVRNLGKPVELAGQYYLDGADEVSFLNITGFRDFPLGDLP
SEQ ID NO:04      ------------------------------------------------------------
SEQ ID NO:08      ------------------------------------------------------------
SEQ ID NO:06      --LVVTKGDQYDVRDHTSSKEVRNLGKPVDLASQYYIDGADEVSFLNITGFRDFPLGDLP
SEQ ID NO:10      ------------------------------------------------------------
SEQ ID NO:12      ------------------------------------------------------------
SEQ ID NO:14      ------------------------------------------------------------
                  301                                                         360
```

FIGURE 1C

```
              *  ***    *  *************************************  **    ********
SEQ ID NO:15     MIQVLRQTSKNVFVPLTVGGIRDFTDASGRYYSSLEVAAEYFRSGA DK MSIGSDAVFAA
SEQ ID NO:02     MLQVLQRASENVFVPLTVGGIRDFTDANGRYYSSLEVASEYFRSGA DK VSIGSDAVYTA
SEQ ID NO:04     ----------------------------------------------  -- -----------
SEQ ID NO:08     ----------------------------------------------  -- -----------
SEQ ID NO:06     MLEVLRCASEKVFVPLTVGGIRDFTDANGRYYSSLEVASEYFRSGA DK ISIGSDAVYAA
SEQ ID NO:10     ----------------------------------------------  -- -----------
SEQ ID NO:12     ----------------------------------------------  -- -----------
SEQ ID NO:14     ----------------------------------------------  -- -----------
                 361                                                          420

** * ******************************************  **    *  ********
SEQ ID NO:15     EEFIKSGVKTGKSSLEQISRVYGNQAVVVSI D PRRVYVNHPDDVPYKVIRVTNPGPNGEE
SEQ ID NO:02     EEYIKTGVKTGKSSIEQISTVYGNQAVVVSI D PRRVYLRKPDEVEFKAIKVSHPGPNGEE
SEQ ID NO:04     ------------------------------- - ----------------------------
SEQ ID NO:08     ------------------------------- - ----------------------------
SEQ ID NO:06     EAFLQTGVKTGKSSLEQISRVYGNQAVVVSI D PRRVYVKSQEDVPFKTVKVSTKGPSGEE
SEQ ID NO:10     ------------------------------- - ----------------------------
SEQ ID NO:12     ------------------------------- - ----------------------------
SEQ ID NO:14     ------------------------------- - ---YVKDPNDVQLKTIRVSSPGSNGEE
                 421                                                          480

*  *  *****************************   *   *** **   ** * ********
SEQ ID NO:15     YAWYQCTVSGGQEGRPIGAFELAKAVEELGAG E ILLNCINC D GQGKGFDIDLVKLISDSV
SEQ ID NO:02     YAWYQCTVNGGREGRPIGAYELAKAVEELGAG E ILLNCIDC D GQGKGFDIDLIKLISDAV
SEQ ID NO:04     -------------------------------- - -------- - ------------------
SEQ ID NO:08     -------------------------------- - -------- - ------------------
SEQ ID NO:06     YAWYQCTVNGGRDSRAIGAYELAKAVEELGAG E ILLNCIDC D GQGCGFDIDLVKMVSDAV
SEQ ID NO:10     -------------------------------- - -------- - ------------------
SEQ ID NO:12     -------------------------------- - -------- - ------------------
SEQ ID NO:14     YAWYQCTVNGGREGRPIGAYELAKAVEELGAG E ILLNCIDC D GQGKGFDVDLIKLISNAV
                 481                                                          540
```

FIGURE 1D

```
              *************  *********  *                          *       ******   * *****
SEQ ID NO:15  GIPVIASSGAGTPDHFSEVFEEDKRICRACCRHFPPERGYQSQSVKEHLQEERIEVRI
SEQ ID NO:02  NIPVIASSGAGVADHFSEVFNETNASAALAAGIFHR-KEVPIKAVKEHLLKEGIEVRL
SEQ ID NO:04  ---------------------------------------------------------
SEQ ID NO:08  ---------------------------------------------------------
SEQ ID NO:06  TIPVIASSGAGAVQHFSEIFEKTNASAALAAGIFHR-KEVPILAVKEHLVNAGVEVRV
SEQ ID NO:10  ---------------------------------------------------------
SEQ ID NO:12  ---------------------------------------------------------
SEQ ID NO:14  SIPVIASXGAGAPEHFSEVFYKTNASAALAAGIFHR-KEVPIQSVKEHLLKEGIEVRI
              541                                                    598
```

PLANT GLUTAMINE AMIDOTRANSFERASE HOMOLOGS

This application claims benefit of Provisional Application No. 60/107,275, filed Nov. 5, 1998.

FIELD OF THE INVENTION

This invention is in the field of plant molecular biology. More specifically, this invention pertains to nucleic acid fragments encoding a histidine biosynthetic protein in plants and seeds.

BACKGROUND OF THE INVENTION

Histidine biosynthesis begins with condensation of ATP with phosphoribosyl pyrophosphate (PRPP) to form $N^1$-(5'-phosphoribosyl)-ATP. Imidazole glycerol phosphate (IGP) synthase, a heterodimeric enzyme consisting of the hisF and hisH gene products, catalyzes the fifth step of histidine biosynthesis, wherein phosphoribulosyl formimino-5-aminoimidazole-4-carboxamide ribonucleotide (PRFAR) and glutamine are transformed into glutamate, IGP and 5-aminoimidazole-4-carboxamide ribonucleotide (AICAR). This reaction is of the glutamine amidotransferase class. AICAR is a purine biosynthetic intermediate; thus there is a linkage between the purine and histidine biosynthetic pathways such that the purine ring removed in the first step of the histidine pathway is replenished by the couple between the reaction catalyzed by IGP synthase and the purine biosynthetic pathway.

It has been shown in a number of systems that missense mutations that decrease, but do not eliminate, the catalytic efficiency of the fourth step (formation of PRFAR from Pro-phoshporibosyl formimino-5-aminoimidazole-4-carboxamide ribonucleotide or 5'-ProFAR, catalyzed by 5'-ProFAR isomerase, the product of the hisA gene) or fifth step of histidine biosynthesis result in a biosynthetic limitation that is overcome by (a) histidine, (b) adenine or (c) a false feedback inhibitor of the first step the histidine pathway (Hartman et al. (1960) *J. Gen. Microbiol.* 22:323; Shedlovsky and Magasanik (1962) *J. Biol. Chem.* 237:3725; Shedlovsky and Magasanik (1962) *J. Biol. Chem* 237:3731; Galloway and Taylor (1980) *J. Bacteriol.* 144:1068; Shioi et al. (1982) *J. Biol. Chem.* 257:7969; Burton (1955) *Biochem. J.* 61:473; Burton (1957) *Biochem. J.* 66:488; Stougaard and Kennedy (1988) *J. Bacteriol.* 170:250). This result indicates that a high level flux through the partially blocked histidine biosynthetic pathway results in an ATP (energy) drain. Such blockage has been shown to have unique, deleterious pleiotropic effects upon a diversity of energy-intensive microbial processes including chemotaxis (Galloway and Taylor (1980) *J. Bacteriol.* 144:1068), DNA replication (Burton (1955) *Biochem. J.* 61:473; Burton (1957) *Biochem. J.* 66:488) and nitrogen fixation (Stougaard and Kennedy (1988) *J. Bacteriol.* 170:250). In each interrupted process, activity is restored by (a) histidine, (b) adenine or (c) a false feedback inhibitor of the first step in histidine biosynthesis.

These studies strongly suggest that enzymes encoded by the hisA, hisF or hisH genes will be useful for discovering herbicides and fungicides. The discovery of homologous biosynthetic pathways and corresponding enzymes in plants and fingi indicates that inhibition of such enzymes would be viable strategies for herbicidal control of unwanted vegetation and fungicidal control of plant disease. For example, inhibition of the fourth and fifth steps of histidine biosynthesis will result in the specific draining of the ATP pool to levels significantly lower than normal (Johnson and Taylor (1993) *Applied Environ. Microbiol.* 59:3509). This specific drain is achieved by having the histidine synthetic pathway operating at a high, near maximal, rate through the relief from allosteric feedback inhibition of the hisG-encoded enzyme, ATP phosphoribosyl transferase. By preventing the release of AICAR by the IGP synthase, the adenylate pool is drained. Although energy homeostasis can be maintained by simply re phosorylation of the adenylate to a high energy state, inhibition of the hisHF or hisA encoded enzymes traps the adenylate as histidine biosynthetic intermediates. Accordingly, lowered flux through the enzymes encoded by hisA and hisHF will cripple the cell's ability to carry out necessary metabolic processes.

Moreover, interruption of other steps in the histidine biosynthetic pathway in plants may also result in plant growth inhibition or death. For example, decrease or elimination of histidinol phosphate aminotransferase encoded by a plant homolog of hisC may inhibit conversion of glutamate to α-ketoglutarate and thereby have a detrimental effect on plant growth and development. The enzyme encoded by hisB is in part responsible for catalyzing the seventh and ninth steps of the histidine biosynthetic pathway. In the seventh step of the pathway D-erythro-1-(imidazol-4-yl) glycerol 3-phosphate is converted to 3-(imidazol-4-yl)-2oxopropyl phosphate by HisB. In the ninth step of the pathway histidinol phosphate is converted to histidinol by the action of HisB. Very little is know about HisB activity in plants, however, because this enzyme catalyzes two steps in the pathway. Interruption of HisB activity could severely alter normal histidine biosynthesis. Lastly, interruption of histidinol dehydrogenase activity (encoded by a homolog of the hisD gene), the enzyme that catalyzes the final step in the pathway, would prevent the formation of histidine. Finally, since the biosynthesis of histidine is energetically costly to the cell, inhibition of transformations at the later steps in the pathway would consume significant cellular energy resources without the formation of the expected end product, thus placing the affected cell at a disadvantage.

Thus, availability of the genes and their encoded enzymes has utility for herbicide and fungicide discovery via the design and implementation of cell-based screening and assay methodologies, enzyme-based screening and assay methodologies, rationale inhibitor design, x-ray crystallography, combinatorial chemistry and other modern biochemical and biotechnological methods.

SUMMARY OF THE INVENTION

The present invention relates to isolated polynucleotides comprising a nucleotide sequence encoding a first polypeptide of at least 60 amino acids that has at least 85% identity based on the Clustal method of alignment when compared to a polypeptide selected from the group consisting of an impatiens glutamine amidotransferase homolog of SEQ ID NO:2, corn glutamine amidotransferase homolog polypeptide of SEQ ID NO:4, SEQ ID NO:6, or SEQ ID NO:8, a rice glutamine amidotransferase homolog polypeptide of SEQ ID NO:10, a soybean glutamine amidotransferase homolog polypeptide of SEQ ID NO:12 or SEQ ID NO:14. The present invention also relates to an isolated polynucleotide comprising the complement of the nucleotide sequences described above.

It is preferred that the isolated polynucleotide of the claimed invention consists of a nucleic acid sequence selected from the group consisting of SEQ ID NOs:1, 3, 5, 7, 9, 11, and 13 that codes for the polypeptide selected from the group consisting of SEQ ID NOs:2, 4, 6, 8, 10, 12, and 14. The present invention also relates to an isolated polynucleotide comprising a nucleotide sequences of at least 40 (preferably at least 30) contiguous nucleotides derived from a nucleotide sequence selected from the group consisting of SEQ ID NOs:1, 3, 5, 7, 9, 11, 13, and the complement of such nucleotide sequences.

The present invention relates to a chimeric gene comprising an isolated polynucleotide of the present invention operably linked to suitable regulatory sequences.

The present invention relates to an isolated host cell comprising a chimeric gene of the present invention or an isolated polynucleotide of the present invention. The host cell may be eukaryotic, such as a yeast or a plant cell, or prokaryotic, such as a bacterial cell. The present invention also relates to a virus, preferably a baculovirus, comprising an isolated polynucleotide of the present invention or a chimeric gene of the present invention.

The present invention relates to a process for producing an isolated host cell comprising a chimeric gene of the present invention or an isolated polynucleotide of the present invention, the process comprising either transforming or transfecting an isolated compatible host cell with a chimeric gene or isolated polynucleotide of the present invention.

The present invention relates to a glutamine amidotransferase homolog polypeptide of at least 60 amino acids comprising at least 85% homology based on the Clustal method of alignment compared to a polypeptide selected from the group consisting of SEQ ID NOs:2, 4, 6, 8, 10, 12, and 14.

The present invention relates to a method of selecting an isolated polynucleotide that affects the level of expression of a glutamine amidotransferase homolog polypeptide in a host cell, preferably a plant cell, the method comprising the steps of:

constructing an isolated polynucleotide of the present invention or an isolated chimeric gene of the present invention;

introducing the isolated polynucleotide or the isolated chimeric gene into a host cell;

measuring the level a glutamine amidotransferase homolog polypeptide in the host cell containing the isolated polynucleotide; and comparing the level of a glutamine amidotransferase homolog polypeptide in the host cell containing the isolated polynucleotide with the level of a glutamine amidotransferase homolog polypeptide in a host cell that does not contain the isolated polynucleotide.

The present invention relates to a method of obtaining a nucleic acid fragment encoding a substantial portion of a glutamine amidotransferase homolog polypeptide gene, preferably a plant glutamine amidotransferase homolog polypeptide gene, comprising the steps of: synthesizing an oligonucleotide primer comprising a nucleotide sequence of at least 60 (preferably at least 40, most preferably at least 30) contiguous nucleotides derived from a nucleotide sequence selected from the group consisting of SEQ ID NOs:1, 3, 5, 7, 9, 11, 13, and the complement of such nucleotide sequences; and amplifying a nucleic acid fragment (preferably a cDNA inserted in a cloning vector) using the oligonucleotide primer. The amplified nucleic acid fragment preferably will encode a portion of a glutamine amidotransferase homolog amino acid sequence.

The present invention also relates to a method of obtaining a nucleic acid fragment encoding all or a substantial portion of the amino acid sequence encoding a glutamine amidotransferase homolog polypeptide comprising the steps of: probing a cDNA or genomic library with an isolated polynucleotide of the present invention; identifying a DNA clone that hybridizes with an isolated polynucleotide of the present invention; isolating the identified DNA clone; and sequencing the cDNA or genomic fragment that comprises the isolated DNA clone.

A further embodiment of the instant invention is a method for evaluating at least one compound for its ability to inhibit the activity of a glutamine amidotransferase homolog, the method comprising the steps of: (a) transforming a host cell with a chimeric gene comprising a nucleic acid fragment encoding a glutamine amidotransferase homolog, operably linked to suitable regulatory sequences; (b) growing the transformed host cell under conditions that are suitable for expression of the chimeric gene wherein expression of the chimeric gene results in production of glutamine amidotransferase homolog in the transformed host cell; (c) optionally purifying the glutamine amidotransferase homolog expressed by the transformed host cell; (d) treating the glutamine amidotransferase homolog with a compound to be tested; and (e) comparing the activity of the glutamine amidotransferase homolog that has been treated with a test compound to the activity of an untreated glutamine amidotransferase homolog, thereby selecting compounds with potential for inhibitory activity.

The present invention relates to a composition comprising an isolated polynucleotide of the present invention.

The present invention relates to an isolated polynucleotide of the present invention comprising the nucleotide sequence comprising at least 30 contiguous nucleotides of a nucleic sequence selected from the group consisting of SEQ ID NOs:1, 3, 5, 7, 9, 11, and 13.

The present invention relates to an expression cassette comprising an isolated polynucleotide of the present invention operably linked to a promoter.

The present invention relates to a method for positive selection of a transformed cell comprising:

(a) transforming a plant cell with the chimeric gene of the present invention or an expression cassette of the present invention; and (b) growing the transformed plant cell, preferably a monocot such as corn, under conditions allowing expression of the polynucleotide in an amount sufficient to complement a histidine biosynthetic auxotroph to provide a positive selection means.

BRIEF DESCRIPTION OF THE DRAWINGS AND SEQUENCE LISTING

The invention can be more fully understood from the following detailed description and the accompanying drawings and Sequence Listing which form a part of this application.

FIGS. 1A–1D shows a comparison of the amino acid sequences of the *Arabidopsis thaliana* glutamine amidotransferase protein having NCBI General Identifier No. 3219164 (SEQ ID NO:15) and the amino acid sequence encoded by the cDNA insert in clone ids.pk0024.c4 (SEQ ID NO:2) encoding an entire glutamine amidotransferase (HisHF) and the amino acid sequences encoding partial glutamine amidotransferases (HisHF) from corn contig assembled from clones cpe1c.pk012.c10, p0010.cbpbq28r, and p0131.ccdap46r (SEQ ID NO:4), corn contig assembled from clones cco1n.pk071.i21, cco1n.pk071.i21:fis, cpj1c.pk005.p14, p0016.ctscc75r, and rlr48.pk0001.f5 (SEQ ID NO:6), corn clone p0119.cmtnx82r (SEQ ID NO:8), rice clone rr1.pk094.n24 (SEQ ID NO:10), soybean clone sdp4c.pk002.n13 (SEQ ID NO:12), and a soybean contig assembled from clones sl1.pk152.c18, sl1.pk152.c18:fis, and src3c.pk022.b14 (SEQ ID NO:14). The predicted CTP cleavage site is indicated with an arrow above the sequences. The carbamoyl-phosphate synthase protein GATASE domain signature E motif 2 and the GATASE type 1 motif are boxed. An asterisk (*) above the alignment indicates those amino acids conserved among impatiens and *Arabidopsis* sequences. The location of the amino acids which when mutagenized effected enzyme activity are indicated by a black box and white letters. Dashes are used by the program to maximize the alignment.

Table 1 lists the polypeptides that are described herein, the designation of the cDNA clones that comprise the nucleic acid fragments encoding polypeptides representing all or a substantial portion of these polypeptides, and the corresponding identifier (SEQ ID NO:) as used in the attached Sequence Listing. The sequence descriptions and Sequence Listing attached hereto comply with the rules governing nucleotide and/or amino acid sequence disclosures in patent applications as set forth in 37 C.F.R. §1.821–1.825.

TABLE 1

Histidine Biosynthetic Enzyme

| Protein | Clone Designation | SEQ ID NO: (Nucleotide) | (Amino Acid) |
|---|---|---|---|
| Impatiens Glutamine Amidotransferase (HisHF) | ids.pk0024.c4:fis | 1 | 2 |
| Corn Glutamine Amidotransferase (HisHF) | Contig of: cpe1c.pk012.c10 p0010.cbpbq28r p0131.ccdap46r | 3 | 4 |
| Corn Glutamine Amidotransferase (HisHF) | Contig of: cco1n.pk071.i21 cco1n.pk071.i21:fis cpj1c.pk005.p14 p0016.ctscc75r rlr48.pk0001.f5* | 5 | 6 |
| Corn Glutamine Amidotransferase (HisHF) | p0119.cmtnx82r | 7 | 8 |
| Rice Glutamine Amidotransferase (HisHF) | rr1.pk094.n24 | 9 | 10 |
| Soybean Glutamine Amidotransferase (HisHF) | sdp4c.pk002.n13 | 11 | 12 |
| Soybean Glutamine Amidotransferase (HisHF) | Contig of: sl1.pk152.c18 sl1.pk152.c18:fis src3c.pk022.b14 | 13 | 14 |

*clone rlr48.pk0001.f5 is in reality a corn clone which was misidentified at the lab.

The Sequence Listing contains the one letter code for nucleotide sequence characters and the three letter codes for amino acids as defined in conformity with the IUPAC-IUBMB standards described in *Nucleic Acids Res.* 13:3021–3030 (1985) and in the *Biochemical J.* 219 (No. 2):345–373 (1984) which are herein incorporated by reference. The symbols and format used for nucleotide and amino acid sequence data comply with the rules set forth in 37 C.F.R. §1.822.

Polynucleotide sequences encoding portions of Glutamine amidotransferases (HisHF) polypeptides from corn (derived from clone ccase-b.pk0024.b9 and a contig assembled from clones cco1n.pk071.i21 and cen3n.pk0211.e9), *Impatiens* (derived from clone ids.pk0024.c4), and soybean (derived from clones sdp4c.001.e7 and sdp4c.pk002.n13) are found in U.S. Provisional Application No. 60/107,275, filed Nov. 5, 1998, incorporated herein by reference.

DETAILED DESCRIPTION OF THE INVENTION

In the context of this disclosure, a number of terms shall be utilized. As used herein, a "polynucleotide" is a nucleotide sequence such as a nucleic acid fragment. A polynucleotide may be a polymer of RNA or DNA that is single- or double-stranded, that optionally contains synthetic, non-natural or altered nucleotide bases. A polynucleotide in the form of a polymer of DNA may be comprised of one or more segments of cDNA, genomic DNA, or synthetic DNA. An isolated polynucleotide of the present invention may include at least 60 contiguous nucleotides, preferably at least 40 contiguous nucleotides, most preferably at least 30 contiguous nucleotides, of the nucleic acid sequence of the SEQ ID NOs:1, 3, 5, 7, 9, 11, and 13.

As used herein, "contig" refers to a nucleotide sequence that is assembled from two or more constituent nucleotide sequences that share common or overlapping regions of sequence homology. For example, the nucleotide sequences of two or more nucleic aced fragments can be compared and aligned in order to identify common or overlapping sequences. Where common or overlapping sequences exist between two or more nucleic acid fragments, the sequences (and thus their corresponding nucleic acid fragments) can be assembled into a single contiguous nucleotide sequence.

As used herein, "substantially similar" refers to nucleic acid fragments wherein changes in one or more nucleotide bases results in substitution of one or more amino acids, but do not affect the functional properties of the polypeptide encoded by the nucleotide sequence. "Substantially similar" also refers to nucleic acid fragments wherein changes in one or more nucleotide bases does not affect the ability of the nucleic acid fragment to mediate alteration of gene expression by gene silencing through for example antisense or co-suppression technology. "Substantially similar" also refers to modifications of the nucleic acid fragments of the instant invention such as deletion or insertion of one or more nucleotides that do not substantially affect the functional properties of the resulting transcript vis-à-vis the ability to mediate gene silencing or alteration of the functional properties of the resulting protein molecule. It is therefore understood that the invention encompasses more than the specific exemplary nucleotide or amino acid sequences and includes functional equivalents thereof.

Substantially similar nucleic acid fragments may be selected by screening nucleic acid fragments representing subfragments or modifications of the nucleic acid fragments of the instant invention, wherein one or more nucleotides are substituted, deleted and/or inserted, for their ability to affect the level of the polypeptide encoded by the unmodified nucleic acid fragment in a plant or plant cell. For example, a substantially similar nucleic acid fragment representing at least 30 contiguous nucleotides derived from the instant nucleic acid fragment can be constructed and introduced into a plant or plant cell. The level of the polypeptide encoded by the unmodified nucleic acid fragment present in a plant or plant cell exposed to the substantially similar nucleic fragment can then be compared to the level of the polypeptide in a plant or plant cell that is not exposed to the substantially similar nucleic acid fragment.

For example, it is well known in the art that antisense suppression and co-suppression of gene expression may be accomplished using nucleic acid fragments representing less than the entire coding region of a gene, and by nucleic acid fragments that do not share 100% sequence identity with the gene to be suppressed. Moreover, alterations in a nucleic acid fragment which result in the production of a chemically equivalent amino acid at a given site, but do not effect the functional properties of the encoded polypeptide, are well known in the art. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the polypeptide molecule would also not be expected to alter the activity of the polypeptide. Each of the proposed modifications is well within the routine skill in the art, as is determination of retention of biological activity of the encoded products. Consequently, an isolated polynucleotide comprising a nucleotide sequence of at least 60 (preferably at least 40, most preferably at least 30) contiguous nucleotides derived from a nucleotide sequence selected from the group consisting of SEQ ID NOs:1, 3, 5, 7, 9, 11, 13, and the complement of such nucleotide sequences may be used in methods of selecting an isolated polynucleotide that affects the expression of a polypeptide in a plant cell. A method of selecting an isolated polynucleotide that affects the level of expression of a polypeptide (such as amido glutamine amidotransferase) in a host cell (eukaryotic, such as plant or yeast, prokaryotic such as bacterial, or viral) may comprise the steps of: constructing an isolated polynucleotide of the present invention or an isolated chimeric gene of the present invention; introducing the isolated polynucleotide or the isolated chimeric gene into a host cell; measuring the level a polypeptide in the host cell containing the isolated polynucleotide; and comparing the level of a polypeptide in the host cell containing the isolated polynucleotide with the level of a polypeptide in a host cell that does not contain the isolated polynucleotide.

Moreover, substantially similar nucleic acid fragments may also be characterized by their ability to hybridize. Estimates of such homology are provided by either DNA-DNA or DNA-RNA hybridization under conditions of stringency as is well understood by those skilled in the art (Hames and Higgins, Eds. (1985) Nucleic Acid Hybridisation, IRL Press, Oxford, U.K.). Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions. One set of preferred conditions uses a series of washes starting with 6×SSC, 0.5% SDS at room temperature for 15 min. then repeated with 2×SSC, 0.5% SDS at 45° C. for 30 min, and then repeated twice with 0.2×SSC, 0.5% SDS at 50° C. for 30 min. A more preferred set of stringent conditions uses higher temperatures in which the washes are identical to those above except for the temperature of the final two 30 min washes in 0.2×SSC, 0.5% SDS was increased to 60° C. Another preferred set of highly stringent conditions uses two final washes in 0.1×SSC, 0.1% SDS at 65° C.

Substantially similar nucleic acid fragments of the instant invention may also be characterized by the percent identity of the amino acid sequences that they encode to the amino acid sequences disclosed herein, as determined by algorithms commonly employed by those skilled in this art. Suitable nucleic acid fragments (isolated polynucleotides of the present invention) encode polypeptides that are at least 70%, preferably at least 80% identical to the amino acid sequences reported herein. Preferred nucleic acid fragments encode amino acid sequences that are at least 85% identical to the amino acid sequences reported herein. More preferred nucleic acid fragments encode amino acid sequences that are at least 90% identical to the amino acid sequences reported herein. Most preferred are nucleic acid fragments that encode amino acid sequences that are at least 95% identical to the amino acid sequences reported herein. Suitable nucleic acid fragments not only have the above homologies but typically encode a polypeptide having at least 50 amino acids, preferably at least 100 amino acids, more preferably at least 150 amino acids, still more preferably at least 200 amino acids, and most preferably at least 250 amino acids. Sequence alignments and percent identity calculations were performed using the Megalign program of the LASERGENE bioinformatics computing suite (DNASTAR Inc., Madison, Wis.). Multiple alignment of the sequences was performed using the Clustal method of alignment (Higgins and Sharp (1989) CABIOS. 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5.

A "substantial portion" of an amino acid or nucleotide sequence comprises an amino acid or a nucleotide sequence that is sufficient to afford putative identification of the protein or gene that the amino acid or nucleotide sequence comprises. Amino acid and nucleotide sequences can be evaluated either manually by one skilled in the art, or by using computer-based sequence comparison and identification tools that employ algorithms such as BLAST (Basic Local Alignment Search Tool; Altschul et al. (1993) J. Mol. Biol. 215:403–410. In general, a sequence of ten or more contiguous amino acids or thirty or more contiguous nucleotides is necessary in order to putatively identify a polypeptide or nucleic acid sequence as homologous to a known protein or gene. Moreover, with respect to nucleotide sequences, gene-specific oligonucleotide probes comprising 30 or more contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12 or more nucleotides may be used as amplification primers in PCR in order to obtain a particular nucleic acid fragment comprising the primers. Accordingly, a "substantial portion" of a nucleotide sequence comprises a nucleotide sequence that will afford specific identification and/or isolation of a nucleic acid fragment comprising the sequence. The instant specification teaches amino acid and nucleotide sequences encoding polypeptides that comprise one or more particular plant proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

"Codon degeneracy" refers to divergence in the genetic code permitting variation of the nucleotide sequence without affecting the amino acid sequence of an encoded polypeptide. Accordingly, the instant invention relates to any nucleic acid fragment comprising a nucleotide sequence that encodes all or a substantial portion of the amino acid sequences set forth herein. The skilled artisan is well aware of the "codon-bias" exhibited by a specific host cell in usage of nucleotide codons to specify a given amino acid. Therefore, when synthesizing a nucleic acid fragment for improved expression in a host cell, it is desirable to design the nucleic acid fragment such that its frequency of codon usage approaches the frequency of preferred codon usage of the host cell.

"Synthetic nucleic acid fragments" can be assembled from oligonucleotide building blocks that are chemically synthesized using procedures known to those skilled in the art. These building blocks are ligated and annealed to form larger nucleic acid fragments which may then be enzymatically assembled to construct the entire desired nucleic acid fragment. "Chemically synthesized", as related to nucleic acid fragment, means that the component nucleotides were assembled in vitro. Manual chemical synthesis of nucleic acid fragments may be accomplished using well established procedures, or automated chemical synthesis can be performed using one of a number of commercially available machines. Accordingly, the nucleic acid fragments can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Gene" refers to a nucleic acid fragment that expresses a specific protein, including regulatory sequences preceding (5' non-coding sequences) and following (3' noncoding sequences) the coding sequence. "Native gene" refers to a gene as found in nature with its own regulatory sequences. "Chimeric gene" refers any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the sa me source, but arranged in a manner different than that found in nature. "Endogenous gene" refers to a native gene in its natural location in the genome of an organism. A "foreign" gene refers to a gene Dot normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Coding sequence" refers to a nucleotide sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" refers to a nucleotide sequence capable of controlling the expression of a coding sequence or functional RNA. In general, a coding sequence is located 3' to a promoter sequence. The promoter sequence consists of proximal and more distal upstream elements, the latter elements often referred to as enhancers. Accordingly, an "enhancer" is a nucleotide sequence which can stimulate promoter activity and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic nucleotide segments. It is understood by those skilled in the art that different promoters may direct the expression of a gene in different tissues or cell types, or at different stages of development, or in response to different environmental conditions. Promoters which cause a nucleic acid fragment to be expressed in most cell types at most times are commonly referred to as "constitutive promoters". New promoters of various types useful in plant cells are constantly being discovered; numerous examples may be found in the compilation by Okamuro and Goldberg (1989) *Biochemistry of Plants* 15:1–82. It is further recognized that since in most cases the exact boundaries of regulatory sequences have not been completely defined, nucleic acid fragments of different lengths may have identical promoter activity.

The "translation leader sequence" refers to a nucleotide sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner and Foster (1995) *Mol. Biotechnol* 3:225–236).

The "3' non-coding sequences" refer to nucleotide sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al. (1989) *Plant Cell* 1:671–680.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA (mRNA)" refers to the RNA that is without introns and that can be translated into polypeptide by the cell. "cDNA" refers to a double-stranded DNA that is complementary to and derived from mRNA. "Sense" RNA refers to an RNA transcript that includes the mRNA and so can be translated into a polypeptide by the cell. "Antisense RNA" refers to an RNA transcript that is complementary to all or part of a target primary transcript or mRNA and that blocks the expression of a target gene (see U.S. Pat. No. 5,107,065, incorporated herein by reference). The complementarity of an antisense RNA may be with any part of the specific nucleotide sequence, i.e., at the 5' non-coding sequence, 3' non-coding sequence, introns, or the coding sequence. "Functional RNA" refers to sense RNA, antisense RNA, ribozyme RNA, or other RNA that may not be translated but yet has an effect on cellular processes.

The term "operably linked" refers to the association of two or more nucleic acid fragments on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. Expression may also refer to translation of mRNA into a polypeptide. "Antisense inhibition" refers to the production of antisense RNA transcripts capable of suppressing the expression of the target protein. "Overexpression" refers to the production of a gene product in transgenic organisms that exceeds levels of production in normal or non-transformed organisms. "Co-suppression" refers to the production of sense RNA transcripts capable of suppressing the expression of identical or substantially similar foreign or endogenous genes (U.S. Pat. No. 5,231,020, incorporated herein by reference).

"Altered levels" refers to the production of gene product(s) in transgenic organisms in amounts or proportions that differ from that of normal or non-transformed organisms.

"Mature" protein refers to a post-translationally processed polypeptide; i.e., one from which any pre- or propeptides present in the primary translation product have been removed. "Precursor" protein refers to the primary product of translation of mRNA; i.e., with pre- and propeptides still present. Pre- and propeptides may be but are not limited to intracellular localization signals.

A "chloroplast transit peptide" is an amino acid sequence which is translated in conjunction with a protein and directs the protein to the chloroplast or other plastid types present in the cell in which the protein is made. "Chloroplast transit sequence" refers to a nucleotide sequence that encodes a chloroplast transit peptide. A "signal peptide" is an amino acid sequence which is translated in conjunction with a protein and directs the protein to the secretory system (Chrispeels (1991) *Ann. Rev. Plant Phys. Plant Mol. Biol.* 42:21–53). If the protein is to be directed to a vacuole, a vacuolar targeting signal (supra) can further be added, or if to the endoplasmic reticulum, an endoplasmic reticulum retention signal (supra) may be added. If the protein is to be directed to the nucleus, any signal peptide present should be removed and instead a nuclear localization signal included (Raikhel (1992) *Plant Phys.* 100:1627–1632).

"Transformation" refers to the transfer of a nucleic acid fragment into the genome of a host organism, resulting in genetically stable inheritance. Host organisms containing the transformed nucleic acid fragments are referred to as "transgenic" organisms. Examples of methods of plant transformation include *Agrobacterium*-mediated transformation (De Blaere et al. (1987) *Meth. Enzymol.* 143:277) and particle-accelerated or "gene gun" transformation technology (Klein et al. (1987) *Nature (London)* 327:70–73; U.S. Pat. No. 4,945,050, incorporated herein by reference).

Standard recombinant DNA and molecular cloning techniques used herein are well known in the art and are described more fully in Sambrook et al. *Molecular Cloning: A Laboratory Manual*; Cold Spring Harbor Laboratory Press: Cold Spring Harbor, 1989 (hereinafter "Maniatis").

Nucleic acid fragments encoding at least a portion of several histidine biosynthetic enzymes have been isolated and identified by comparison of random plant cDNA sequences to public databases containing nucleotide and protein sequences using the BLAST algorithms well known to those skilled in the art. The nucleic acid fragments of the instant invention may be used to isolate cDNAs and genes encoding homologous proteins from the same or other plant species. Isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g., polymerase chain reaction, ligase chain reaction).

For example, genes encoding other glutamine amidotransferase homologs, either as cDNAs or genomic DNAs, could be isolated directly by using all or a portion of the instant nucleic acid fragments as DNA hybridization probes to screen libraries from any desired plant employing methodology well known to those skilled in the art. Specific oligonucleotide probes based upon the instant nucleic acid sequences can be designed and synthesized by methods known in the art (Maniatis). Moreover, the entire sequences can be used directly to synthesize DNA probes by methods known to the skilled artisan such as random primer DNA labeling, nick translation, or end-labeling techniques, or RNA probes using available in vitro transcription systems. In addition, specific primers can be designed and used to amplify a part or all of the instant sequences. The resulting amplification products can be labeled directly during amplification reactions or labeled after amplification reactions, and used as probes to isolate full length cDNA or genomic fragments under conditions of appropriate stringency.

In addition, two short segments of the instant nucleic acid fragments may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding plant genes. Alternatively, the second primer sequence may be based upon sequences derived from the cloning vector. For example, the skilled artisan can follow the RACE protocol (Frohman et al. (1988) *Proc. Natl. Acad. Sci. USA* 85:8998–9002) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (BRL), specific 3' or 5' cDNA fragments can be isolated (Ohara et al. (1989) *Proc. Natl. Acad. Sci. USA* 86:5673–5677; Loh et al. (1989) *Science* 243:217–220). Products generated by the 3' and 5' RACE procedures can be combined to generate full-length cDNAs (Frohman and Martin (1989) *Techniques* 1:165). Consequently, a polynucleotide comprising a nucleotide sequence of at least 60 (preferably at least 40, most preferably one of at least 30) contiguous nucleotides derived from a nucleotide sequence selected from the group consisting of SEQ ID NOs:1, 3, 5, 7, 9, 11, 13, and the complement of such nucleotide sequences may be used in such methods to obtain a nucleic acid fragment encoding a substantial portion of an amino acid sequence of a polypeptide. The present invention relates to a method of obtaining a nucleic acid fragment encoding a substantial portion of a polypeptide of a gene (such as a glutamine amidotransferase homolog) preferably a substantial portion of a plant polypeptide of a gene, comprising the steps of: synthesizing an oligonucleotide primer comprising a nucleotide sequence of at least 60 (preferably at least 40, most preferably at least 30) contiguous nucleotides derived from a nucleotide sequence selected from the group consisting of SEQ ID NOs:1, 3, 5, 7, 9, 11, 13, and the complement of such nucleotide sequences; and amplifying a nucleic acid fragment (preferably a cDNA inserted in a cloning vector) using the oligonucleotide primer. The amplified nucleic acid fragment preferably will encode a portion of a polypeptide.

Availability of the instant nucleotide and deduced amino acid sequences facilitates immunological screening of cDNA expression libraries. Synthetic peptides representing portions of the instant amino acid sequences may be synthesized. These peptides can be used to immunize animals to produce polyclonal or monoclonal antibodies with specificity for peptides or proteins comprising the amino acid sequences. These antibodies can be then be used to screen cDNA expression libraries to isolate full-length cDNA clones of interest (Lemer (1984) Adv. Immunol. 36:1–34; Maniatis).

The nucleic acid fragments of the instant invention may be used to create transgenic plants in which the disclosed polypeptides are present at higher or lower levels than normal or in cell types or developmental stages in which they are not normally found. This would have the effect of altering the level of histidine biosynthesis in those cells.

Overexpression of the proteins of the instant invention may be accomplished by first constructing a chimeric gene in which the coding region is operably linked to a promoter capable of directing expression of a gene in the desired tissues at the desired stage of development. For reasons of convenience, the chimeric gene may comprise promoter sequences and translation leader sequences derived from the same genes. 3' Non-coding sequences encoding transcription termination signals may also be provided. The instant chimeric gene may also comprise one or more introns in order to facilitate gene expression.

Plasmid vectors comprising the instant chimeric gene can then be constructed. The choice of plasmid vector is dependent upon the method that will be used to transform host plants. The skilled artisan is well aware of the genetic elements that must be present on the plasmid vector in order to successfully transform, select and propagate host cells containing the chimeric gene. The skilled artisan will also recognize that different independent transformation events will result in different levels and patterns of expression (Jones et al. (1985) EMBO J. 4:2411–2418; De Almeida et al. (1989) Mol. Gen Genetics 218:78–86), and thus that multiple events must be screened in order to obtain lines displaying the desired expression level and pattern. Such screening may be accomplished by Southern analysis of DNA, Northern analysis of mRNA expression, Western analysis of protein expression, or phenotypic analysis. For some applications it may be useful to direct the instant polypeptides to different cellular compartments, or to facilitate their secretion from the cell. It is thus envisioned that the chimeric gene described above may be further supplemented by altering the coding sequence to encode the instant polypeptides with appropriate intracellular targeting sequences such as transit sequences (Keegstra (1989) Cell 56:247–253), signal sequences or sequences encoding endoplasmic reticulum localization (Chrispeels (1991) Ann. Rev. Plant Phys. Plant Mol. Biol. 42:21–53), or nuclear localization signals (Raikhel (1992) Plant Phys. 100: 1627–1632) added and/or with targeting sequences that are already present removed. While the references cited give examples of each of these, the list is not exhaustive and more targeting signals of utility may be discovered in the future.

It may also be desirable to reduce or eliminate expression of genes encoding the instant polypeptides in plants for some applications. In order to accomplish this, a chimeric gene designed for co-suppression of the instant polypeptide can be constructed by linking a gene or gene fragment encoding that polypeptide to plant promoter sequences. Alternatively, a chimeric gene designed to express antisense RNA for all or part of the instant nucleic acid fragment can be constructed by linking the gene or gene fragment in reverse orientation to plant promoter sequences. Either the co-suppression or antisense chimeric genes could be introduced into plants via transformation wherein expression of the corresponding endogenous genes are reduced or eliminated.

Molecular genetic solutions to the generation of plants with altered gene expression have a decided advantage over more traditional plant breeding approaches. Changes in plant phenotypes can be produced by specifically inhibiting expression of one or more genes by antisense inhibition or cosuppression (U.S. Pat. Nos. 5,190,931, 5,107,065 and 5,283,323). An antisense or cosuppression construct would act as a dominant negative regulator of gene activity. While conventional mutations can yield negative regulation of gene activity these effects are most likely recessive. The dominant negative regulation available with a transgenic approach may be advantageous from a breeding perspective. In addition, the ability to restrict the expression of specific phenotype to the reproductive tissues of the plant by the use of tissue specific promoters may confer agronomic advantages relative to conventional mutations which may have an effect in all tissues in which a mutant gene is ordinarily expressed.

The person skilled in the art will know that special considerations are associated with the use of antisense or cosuppression technologies in order to reduce expression of particular genes. For example, the proper level of expression of sense or antisense genes may require the use of different chimeric genes utilizing different regulatory elements known to the skilled artisan. Once transgenic plants are obtained by one of the methods described above, it will be necessary to screen individual transgenics for those that most effectively display the desired phenotype. Accordingly, the skilled artisan will develop methods for screening large numbers of transformants. The nature of these screens will generally be chosen on practical grounds, and is not an inherent part of the invention. For example, one can screen by looking for changes in gene expression by using antibodies specific for the protein encoded by the gene being suppressed, or one could establish assays that specifically measure enzyme activity. A preferred method will be one which allows large numbers of samples to be processed rapidly, since it will be expected that a large number of transformants will be negative for the desired phenotype.

The instant polypeptides (or portions thereof) may be produced in heterologous host cells, particularly in the cells of microbial hosts, and can be used to prepare antibodies to the these proteins by methods well known to those skilled in the art. The antibodies are useful for detecting the polypeptides of the instant invention in situ in cells or in vitro in cell extracts. Preferred heterologous host cells for production of the instant polypeptides are microbial hosts. Microbial expression systems and expression vectors containing regulatory sequences that direct high level expression of foreign proteins are well known to those skilled in the art. Any of these could be used to construct a chimeric gene for production of the instant polypeptides. This chimeric gene could then be introduced into appropriate microorganisms via transformation to provide high level expression of the encoded histidine biosynthetic protein. An example of a vector for high level expression of the instant polypeptides in a bacterial host is provided (Example 6).

Additionally, the instant polypeptides can be used as targets to facilitate design and/or identification of inhibitors of those enzymes that may be useful as herbicides. This is desirable because the polypeptides described herein catalyze a critical step in histidine biosynthesis. Accordingly, inhibition of the activity of one or more of the enzymes described herein could lead to inhibition of plant growth. Thus, the instant polypeptides could be appropriate for new herbicide discovery and design.

All or a substantial portion of the nucleic acid fragments of the instant invention may also be used as probes for genetically and physically mapping the genes that they are a part of, and as markers for traits linked to those genes. Such information may be useful in plant breeding in order to develop lines with desired phenotypes. For example, the instant nucleic acid fragments may be used as restriction fragment length polymorphism (RFLP) markers. Southern blots (Maniatis) of restriction-digested plant genomic DNA may be probed with the nucleic acid fragments of the instant invention. The resulting banding patterns may then be subjected to genetic analyses using computer programs such as MapMaker (Lander et al. (1987) *Genomics* 1:174–181) in order to construct a genetic map. In addition, the nucleic acid fragments of the instant invention may be used to probe Southern blots containing restriction endonuclease-treated genomic DNAs of a set of individuals representing parent and progeny of a defined genetic cross. Segregation of the DNA polymorphisms is noted and used to calculate the position of the instant nucleic acid sequence in the genetic map previously obtained using this population (Botstein et al. (1980) *Am J. Hum. Genet.* 32:314–331).

The production and use of plant gene-derived probes for use in genetic mapping is described in Bematzky and Tanksley (1986) *Plant Mol. Biol. Reporter* 4:3741. Numerous publications describe genetic mapping of specific cDNA clones using the methodology outlined above or variations thereof. For example, F2 intercross populations, backcross populations, randomly mated populations, near isogenic lines, and other sets of individuals may be used for mapping. Such methodologies are well known to those skilled in the art Nucleic acid probes derived from the instant nucleic acid sequences may also be used for physical mapping (i.e., placement of sequences on physical maps; see Hoheisel et al. In: *Nonmammalian Genomic Analysis: A Practical Guide*, Academic press 1996, pp. 319–346, and references cited therein).

In another embodiment, nucleic acid probes derived from the instant nucleic acid sequences may be used in direct fluorescence in situ hybridization (FISH) mapping (Trask (1991) *Trends Genet.* 7:149–154). Although current methods of FISH mapping favor use of large clones (several to several hundred KB; see Laan et al. (1995) *Genome Res.* 5:13–20), improvements in sensitivity may allow performance of FISH mapping using shorter probes.

A variety of nucleic acid amplification-based methods of genetic and physical mapping may be carried out using the instant nucleic acid sequences. Examples include allele-specific amplification (Kazazian (1989) *J. Lab. Clin. Med* 11:95–96), polymorphism of PCR-amplified fragments (CAPS; Sheffield et al. (1993) *Genomics* 16:325–332), allele-specific ligation (Landegren et al. (1988) *Science* 241:1077–1080), nucleotide extension reactions (Sokolov (1990) *Nucleic Acid Res.* 18:3671), Radiation Hybrid Mapping (Walter et al. (1997) *Nat. Genet.* 7:22–28) and Happy Mapping (Dear and Cook (1989) *Nucleic Acid Res.* 17:6795–6807). For these methods, the sequence of a nucleic acid fragment is used to design and produce primer pairs for use in the amplification reaction or in primer extension reactions. The design of such primers is well known to those skilled in the art. In methods employing PCR-based genetic mapping, it may be necessary to identify DNA sequence differences between the parents of the mapping cross in the region corresponding to the instant nucleic acid sequence. This, however, is generally not necessary for mapping methods.

Loss of function mutant phenotypes may be identified for the instant cDNA clones either by targeted gene disruption protocols or by identifying specific mutants for these genes contained in a maize population carrying mutations in all possible genes (Ballinger and Benzer (1989) *Proc. Natl. Acad Sci USA* 86:9402–9406; Koes et al. (1995) *Proc. Natl. Acad Sci USA* 92:8149–8153; Bensen et al. (1995) *Plant Cell* 7:75–84). The latter approach may be accomplished in two ways. First, short segments of the instant nucleic acid fragments may be used in polymerase chain reaction protocols in conjunction with a mutation tag sequence primer on DNAs prepared from a population of plants in which Mutator transposons or some other mutation-causing DNA element has been introduced (see Bensen, supra). The amplification of a specific DNA fragment with these primers indicates the insertion of the mutation tag element in or near the plant gene encoding the instant polypeptides. Alternatively, the instant nucleic acid fragment may be used as a hybridization probe against PCR amplification products generated from the mutation population using the mutation tag sequence primer in conjunction with an arbitrary genomic site primer, such as that for a restriction enzyme site-anchored synthetic adaptor. With either method, a plant containing a mutation in the endogenous gene encoding the instant polypeptides can be identified and obtained. This mutant plant can then be used to determine or confirm the natural function of the instant polypeptides disclosed herein.

EXAMPLES

The present invention is further defined in the following Examples, in which all parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

Example 1

Composition of cDNA Libraries; Isolation and Sequencing of cDNA Clones cDNA libraries representing mRNAs from various impatiens, corn, rice, and soybean tissues were prepared. The characteristics of the libraries are described below.

TABLE 2 cDNA Libraries from Impatiens, Corn, Rice, and Soybean

| Library | Tissue | Clone |
|---------|--------|-------|
| ccoln | Corn Cob of 67 Day Old Plants Grown in Green House[a] | ccoln.pk071.i21 |
| cpe1c | Corn pooled BMS treated with chemicals related to phosphatase[b] | cpe1c.pk012.c10 |
| cpj1c | Corn Pooled BMS Treated With Chemicals Related to Membrane Ionic Force[c] | cpj1c.pk005.p14 |
| ids | *Impatiens balsamia* Developing Seed | ids.pk0024.c4 |
| p0010 | Corn Log Phase Suspension Cells Treated With A23187[d] to Induce Mass Apoptosis | p0010.cbpbq28r |
| p0016 | Corn Tassel Shoots, Pooled, 0.1–1.4 cm | p0016.ctscc75r |
| p0119 | Corn V12-Stage[e] Ear Shoot With Husk, Night Harvested[a] | p0119.cmtnx82r |
| p0131 | Transformed Callus Tissue[a] | p0131.ccdap46r |
| cen3n[f] | Corn Endosperm 20 Days After Pollination[a] | rlr48.pk0001.f5 |
| rr1 | Rice Root of Two Week Old Developing Seedling | rr1.pk094.n24 |
| sdp4c | Soybean Developing Pods (10–12 mm) | sdp4c.pk002.n13 |
| sl1 | Soybean Two-Week-Old Developing Seedlings | sl1.pk152.c18 |
| sl1 | Soybean Two-Week-Old Developing Seedlings | sl1.pk152.c18 |
| src3c | Soybean 8 Day Old Root Infected With Cyst Nematode | src3c.pk022.b14 |

[a]These libraries were normalized essentially as described in U.S. Pat. No. 5,482,845, incorporated herein by reference.
[b]Chemicals used included okadaic acid, cyclosporin A, calyculin A, cypermethrin.
[c]Chemicals used included valinomycin, bafilomycin A1, oligomycin, ionomycin.
[d]A23187 is commercially available from several vendors including Calbiochem.
[e]Corn developmental stages are explained in the publication "How a corn plant develops" from the Iowa State University Coop. Ext. Service Special Report No. 48 reprinted June 1993.
[f]This clone was mislabeled during processing. It belongs to the cen3n library even though it is labeled as a rlr48 clone.

cDNA libraries may be prepared by any one of many methods available. For example, the cDNAs may be introduced into plasmid vectors by first preparing the cDNA libraries in Uni-ZAP™ XR vectors according to the manufacturer's protocol (Stratagene Cloning Systems, La Jolla, Calif.). The Uni-ZAP™ XR libraries are converted into plasmid libraries according to the protocol provided by Stratagene. Upon conversion, cDNA inserts will be contained in the plasmid vector pBluescript. In addition, the cDNAs may be introduced directly into precut Bluescript II SK(+) vectors (Stratagene) using T4 DNA ligase (New England Biolabs), followed by transfection into DH10B cells according to the manufacturer's protocol (GIBCO BRL Products). Once the cDNA inserts are in plasmid vectors, plasmid DNAs are prepared from randomly picked bacterial colonies containing recombinant pBluescript plasmids, or the insert cDNA sequences are amplified via polymerase chain reaction using primers specific for vector sequences flanking the inserted cDNA sequences. Amplified insert DNAs or plasmid DNAs are sequenced in dye-primer sequencing reactions to generate partial cDNA sequences (expressed sequence tags or "ESTs"; see Adams et al., (1991) *Science* 252:1651–1656). The resulting ESTs are analyzed using a Perkin Elmer Model 377 fluorescent sequencer.

Example 2

Identification of cDNA Clones cDNA clones encoding histidine biosynthetic enzymes were identified by conducting BLAST (Basic Local Alignment Search Tool; Altschul et al. (1993) *J. Mol. Biol.* 215:403–410 searches for similarity to sequences contained in the BLAST "nr" database (comprising all non-redundant GenBank CDS translations, sequences derived from the 3-dimensional structure Brookhaven Protein Data Bank, EDIT (the last major release of the SWISS-PROT protein sequence database, EMBL, and DDBJ databases). The cDNA sequences obtained in Example 1 were analyzed for similarity to all publicly available DNA sequences contained in the "nr" database using the BLASTN algorithm provided by the National Center for Biotechnology Information (NCBI). The DNA sequences were translated in all reading frames and compared for similarity to all publicly available protein sequences contained in the "nr" database using the BLASTX algorithm (Gish and States (1993) *Nat. Genet.* 3:266–272) provided by the NCBI. For convenience, the P-value (probability) of observing a match of a cDNA sequence to a sequence contained in the searched databases merely by chance as calculated by BLAST are reported herein as "pLog" values, which represent the negative of the logarithm of the reported P-value. Accordingly, the greater the pLog value, the greater the likelihood that the cDNA sequence and the BLAST "hit" represent homologous proteins.

Example 3

Characterization of cDNA Clones Encoding Glutamine Amidotransferase

The BLASTX search using the EST sequences from clones listed in Table 3 revealed similarity of the polypeptide with similarity to glutamine amidotransferase/cyclase obtained from the translation of the EU *Arabidopsis thaliana* sequencing project (NCBI General Identifier No. 4455213) and to the glutamine amidotransferase/cyclase from *Arabidopsis thaliana* (NCBI General Identifier No. 3219164). Shown in Table 3 are the BLAST results for individual ESTs ("ESrT"), contigs assembled from two or more ESTs ("Contig"), contigs assembled from the sequence of the entire cDNA insert comprising the indicated cDNA clones ("FIS") and one or more ESTs ("Contig*"), Or sequences encoding the entire protein derived from an FIS ("CGS"):

TABLE 3

BLAST Results for Sequences Encoding Polypeptides Homologous to Glutamine Amidotransferase

| | | BLAST pLog Score | |
|---|---|---|---|
| Clone | Status | 4455213 | 3219164 |
| ids.pk0024.c4 | CGS | 254.00 | 254.00 |
| Contig of: cpe1c.pk012.c10 p0010.cbpbq28r p0131.ccdap46r | Contig | 21.00 | 20.40 |
| Contig of: ccoln.pk071.i21 cpj1c.pk005.p14 p0016.ctscc75r rlr48.pk0001.f5 | Contig* | 163.00 | 149.00 |
| p0119.cmtnx82r | EST | 13.00 | 13.00 |
| rr1.pk094.n24 | EST | 19.20 | 18.50 |
| sdp4c.pk002.n13 | EST | 25.40 | 24.70 |
| Contig of: sl1.pk152.c18 sl1.pk152.c18 src3c.pk022.b14 | Contig* | 76.20 | 58.40 |

FIG. 1 presents an alignment of the amino acid sequences set forth in SEQ ID NO:2 and the *Arabidopsis thaliana* sequence (SEQ ID NO:15) and the amino acid sequences from corn contig assembled from clones cpe1c.pk012.c10, p00.10.cbpbg28r, and p0131.ccdap46r (SEQ ID NO:4), corn contig assembled from clones cco1n.pk071.i21, cco1n.pk071.i21:fis, cpj1c.pk005.p14. p0016.ctscc75r, and rlr48.pk0001.f5 (SEQ ID NO:6), corn clone p0119.cmtnx82r (SEQ ID NO:8), rice clone rr1.pk094.n24 (SEQ ID NO:10), soybean clone sdp4c.pk002.n13 (SEQ ID NO:12), and soybean contig assembled from clones sl1.pk152.c18, sl1.pk152.c18:fis, and src3c.pk022.b14 (SEQ ID NO:14). Indicated with an arrow above the sequences is the location of the predicted CTP cleavage site. Boxed are the carbamoyl-phosphate synthase protein GATASE domain signature E motif 2 (probably containing the active Cysteine) and the GTASE type 1 domain. An asterisk (*) above the alignment indicates those amino acids conserved among the impatiens and *Arabidosis* sequences. The location of the amino acids which when mutagenized effected enzyme activity are indicated by a black box and white letters.

The data in Table 4 represents a calculation of the percent identity of the amino acid sequences set forth in SEQ ID NOs:2, 4, 6, 8, 10, 12, and 14 and the *Arabidopsis thaliana* sequence (SEQ ID NO:15).

TABLE 4

Percent Identity of Amino Acid Sequences Deduced From the Nucleotide Sequences of cDNA Clones Encoding Polypeptides Homologous to Glutamine Amidotransferase

| SEQ ID NO. | Percent Identity to 3219164 |
|---|---|
| 2 | 72.9 |
| 4 | 44.6 |
| 6 | 72.5 |
| 8 | 46.5 |
| 10 | 47.1 |
| 12 | 79.3 |
| 14 | 66.7 |

Sequence alignments and percent identity calculations were performed using the Megalign program of the LASERGENE bioinformatics computing suite (DNASTAR Inc., Madison, Wis.). Multiple alignment of the sequences was performed using the Clustal method of alignment (Higgins and Sharp (1989) *CABIOS*. 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5. Sequence alignments and BLAST scores and probabilities indicate that the nucleic acid fragments comprising the instant cDNA clones encode a substantial portion of one impatiens, three corn, one rice and two soybean glutamine amidotransferase. These sequences represent the first monocot, impatiens, and soybean sequences encoding glutamine amidotransferase.

Example 4

Expression of Chimeric Genes in Monocot Cells

A chimeric gene comprising a cDNA encoding the instant polypeptides in sense orientation with respect to the maize 27 kD zein promoter that is located 5' to the cDNA fragment, and the 10 kD zein 3' end that is located 3' to the cDNA fragment, can be constructed. The cDNA fragment of this gene may be generated by polymerase chain reaction (PCR) of the cDNA clone using appropriate oligonucleotide primers. Cloning sites (NcoI or SmaI) can be incorporated into the oligonucleotides to provide proper orientation of the DNA fragment when inserted into the digested vector pML103 as described below. Amplification is then performed in a standard PCR. The amplified DNA is then digested with restriction enzymes NcoI and SmaI and fractionated on an agarose gel. The appropriate band can be isolated from the gel and combined with a 4.9 kb NcoI-SmaI fragment of the plasmid pML103. Plasmid pML103 has been deposited under the terms of the Budapest Treaty at ATCC (American Type Culture Collection, 10801 University Blvd., Manassas, VA 20110-2209), and bears accession number ATCC 97366. The DNA segment from pML103 contains a 1.05 kb SalU-NcoI promoter fragment of the maize 27 kD zein gene and a 0.96 kb SmaI-SalI fragment from the 3' end of the maize 10 kD zein gene in the vector pGem9Zf(+) (Promega). Vector and insert DNA can be ligated at 15° C. overnight, essentially as described (Maniatis). The ligated DNA may then be used to transform *E. coli* XL1-Blue (Epicurian Coli XL-1 Blues; Stratagene). Bacterial transformants can be screened by restriction enzyme digestion of plasmid DNA and limited nucleotide sequence analysis using the dideoxy chain termination method (Sequenase™ DNA Sequencing Kit; U.S. Biochemical). The resulting plasmid construct would comprise a chimeric gene encoding, in the 5' to 3' direction, the maize 27 kD zein promoter, a cDNA fragment encoding the instant polypeptides, and the 10 kD zein 3' region.

The chimeric gene described above can then be introduced into corn cells by the following procedure. Immature corn embryos can be dissected from developing caryopses derived from crosses of the inbred corn lines H99 and LH132. The embryos are isolated 10 to 11 days after pollination when they are 1.0 to 1.5 mm long. The embryos are then placed with the axis-side facing down and in contact with agarose-solidified N6 medium (Chu et al. (1975) *Sci. Sin. Peking* 18:659–668). The embryos are kept in the dark at 27° C. Friable embryogenic callus consisting of undifferentiated masses of cells with somatic proembryoids and embryoids borne on suspensor structures proliferates from the scutellum of these immature embryos. The embryogenic callus isolated from the primary explant can be cultured on N6 medium and sub-cultured on this medium every 2 to 3 weeks.

The plasmid, p35S/Ac (obtained from Dr. Peter Eckes, Hoechst Ag, Frankfurt, Germany) may be used in transformation experiments in order to provide for a selectable marker. This plasmid contains the Pat gene (see European Patent Publication 0 242 236) which encodes phosphinothricin acetyl transferase (PAT). The enzyme PAT confers resistance to herbicidal glutamine synthetase inhibitors such as phosphinothricin. The pat gene in p35S/Ac is under the control of the 35S promoter from Cauliflower Mosaic Virus (Odell et al. (1985) *Nature* 313:810–812) and the 3' region of the nopaline synthase gene from the T-DNA of the Ti plasmid of *Agrobacterium tumefaciens*.

The particle bombardment method (Klein et al. (1987) *Nature* 327:70–73) may be used to transfer genes to the callus culture cells. According to this method, gold particles (1 μm in diameter) are coated with DNA using the following technique. Ten jig of plasmid DNAs are added to 50 μL of a suspension of gold particles (60 mg per mL). Calcium chloride (50 μL of a 2.5 M solution) and spermidine free base (20 μL of a 1.0 M solution) are added to the particles. The suspension is vortexed during the addition of these solutions. After 10 minutes, the tubes are briefly centrifuged (5 sec at 15,000 rpm) and the supernatant removed. The particles are resuspended in 200 µL of absolute ethanol, centrifuged again and the supernatant removed. The ethanol rinse is performed again and the particles resuspended in a final volume of 30 µL of ethanol. An aliquot (5 µL) of the DNA-coated gold particles can be placed in the center of a Kapton™ flying disc (Bio-Rad Labs). The particles are then accelerated into the corn tissue with a Biolistic™ PDS-1000/He (Bio-Rad Instruments, Hercules Calif.), using a helium pressure of 1000 psi, a gap distance of 0.5 cm and a flying distance of 1.0 cm.

For bombardment, the embryogenic tissue is placed on filter paper over agarose-solidified N6 medium. The tissue is arranged as a thin lawn and covered a circular area of about 5 cm in diameter. The petri dish containing the tissue can be placed in the chamber of the PDS-1000/He approximately 8 cm from the stopping screen. The air in the chamber is then evacuated to a vacuum of 28 inches of Hg. The macrocarrier is accelerated with a helium shock wave using a rupture membrane that bursts when the He pressure in the shock tube reaches 1000 psi.

Seven days after bombardment the tissue can be transferred to N6 medium that contains gluphosinate (2 mg per liter) and lacks casein or proline. The tissue continues to grow slowly on this medium. After an additional 2 weeks the tissue can, be transferred to fresh N6 medium containing gluphosinate. After 6 weeks, areas of about 1 cm in diameter of actively growing callus can be identified on some of the plates containing the glufosinate-supplemented medium. These calli may continue to grow when sub-cultured on the selective medium.

Plants can be regenerated from the transgenic callus by first transferring clusters of tissue to N6 medium supplemented with 0.2 mg per liter of 2,4-D. After two weeks the tissue can be transferred to regeneration medium (Fromm et al. (1990) *Bio/Technology* 8:833–839).

Example 5

Expression of Chimeric Genes in Dicot Cells

A seed-specific expression cassette composed of the promoter and transcription terminator from the gene encoding the P subunit of the seed storage protein phaseolin from the bean *Phaseolus vulgaris* (Doyle et al. (1986) *J. Biol. Chem.* 261:9228–9238) can be used for expression of the instant polypeptides in transformed soybean. The phaseolin cassette includes about 500 nucleotides upstream (5') from the translation initiation codon and about 1650 nucleotides downstream (3') from the translation stop codon of phaseolin. Between the 5' and 3' regions are the unique restriction endonuclease sites Nco I (which includes the ATG translation initiation codon), Sma I, Kpn I and Xba I. The entire cassette is flanked by Hind III sites.

The cDNA fragment of this gene may be generated by polymerase chain reaction (PCR) of the cDNA clone using appropriate oligonucleotide primers. Cloning sites can be incorporated into the oligonucleotides to provide proper orientation of the DNA fragment when inserted into the expression vector. Amplification is then performed as described above, and the isolated fragment is inserted into a pUC18 vector carrying the seed expression cassette.

Soybean embryos may then be transformed within the expression vector comprising sequences encoding the instant polypeptides. To induce somatic embryos, cotyledons, 3–5 mm in length dissected from surface sterilized, immature seeds of the soybean cultivar A2872, can be cultured in the light or dark at 26° C. on an appropriate agar medium for 6–10 weeks. Somatic embryos which produce secondary embryos are then excised and placed into a suitable liquid medium. After repeated selection for clusters of somatic embryos which multiplied as early, globular staged embryos, the suspensions are maintained as described below.

Soybean embryogenic suspension cultures can maintained in 35 mL liquid media on a rotary shaker, 150 rpm, at 26° C. with florescent lights on a 16:8 hour day/night schedule. Cultures are subcultured every two weeks by inoculating approximately 35 mg of tissue into 35 mL of liquid medium.

Soybean embryogenic suspension cultures may then be transformed by method of particle gun bombardment (Klein et al. (1987) *Nature* (London) 327:70–73, U.S. Pat. No. 4,945,050). A DuPont Biolistic™ PDS 1000/HE instrument (helium retrofit) can be used for these transformations.

A selectable marker gene which can be used to facilitate soybean transformation is a chimeric gene composed of the 35S promoter from Cauliflower Mosaic Virus (Odell et al. (1985) *Nature* 313:810–812), the hygromycin phosphotransferase gene from plasmid pJR225 (from *E. coli*; Gritz et al. (1983) *Gene* 25:179–188) and the 3' region of the nopaline synthase gene from the T-DNA of the Ti plasmid of *Agrobacterium tumefaciens*. The seed expression cassette comprising the phaseolin 5' region, the fragment encoding the instant polypeptides and the phaseolin 3' region can be isolated as a restriction fragment. This fragment can then be inserted into a unique restriction site of the vector carrying the marker gene.

To 50 µL of a 60 mg/mL 1 µm gold particle suspension is added (in order): 5 µL DNA (1 µg/1 µL), 20 µl spermidine (0.1 M), and 50 µL CaCl$_2$ (2.5 M). The particle preparation is then agitated for three minutes, spun in a microfuge for 10 seconds and the supernatant removed. The DNA-coated particles are then washed once in 400 µL 70% ethanol and resuspended in 40 µL of anhydrous ethanol. The DNA/particle suspension can be sonicated three times for one second each. Five µL of the DNA-coated gold particles are then loaded on each macro carrier disk.

Approximately 300–400 mg of a two-week-old suspension culture is placed in an empty 60×15 mm petri dish and the residual liquid removed from the tissue with a pipette. For each transformation experiment, approximately 5–10 plates of tissue are normally bombarded. Membrane rupture pressure is set at 1100 psi and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post bombardment with fresh media containing 50 mg/mL hygromycin. This selective media can be refreshed weekly. Seven to eight weeks post bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

Example 6

Expression of Chimeric Genes in Microbial Cells

The cDNAs encoding the instant polypeptides can be inserted into the T7 E. coli expression vector pB T430. This vector is a derivative of pET-3a (Rosenberg et A. (1987) Gene 56:125–135) which employs the bacteriophage T7 RNA polymerase/T7 promoter system. Plasmid pBT430 was constructed by first destroying the EcoR I and Hind III sites in pET-3a at their original positions. An oligonucleotide adaptor containing EcoR I and Hind III sites was inserted at the BamH I site of pET-3a. This created pET-3aM with additional unique cloning sites for insertion of genes into the expression vector. Then, the Nde I site at the position of translation initiation was converted to an Nco I site using oligonucleotide-directed mutagenesis. The DNA sequence of pET-3aM in this region, 5'-CATATGG, was converted to 5'-CCCATGG in pBT430.

Plasmid DNA containing a cDNA may be appropriately digested to release a nucleic acid fragment encoding the protein. This fragment may then be purified on a 1% NuSieve GTG" low melting agarose gel (FMC). Buffer and agarose contain 10 $\mu$g/ml ethidium bromide for visualization of the DNA fragment. The fragment can then be purified from the agarose gel by digestion with GELase™ (Epicentre Technologies) according to the manufacturer's instructions, ethanol precipitated, dried and resuspended in 20 $\mu$L of water. Appropriate oligonucleotide adapters may be ligated to the fragment using T4 DNA ligase (New England Biolabs, Beverly, Mass.). The fragment containing the ligated adapters can be purified from the excess adapters using low melting agarose as described above. The vector pBT430 is digested, dephosphorylated with alkaline phosphatase (NEB) and deproteinized with phenol/chloroform as described above. The prepared vector pBT430 and fragment can then be ligated at 16° C. for 15 hours followed by transformation into DH5 electrocompetent cells (GIBCO BRL). Transformants can be selected on agar plates containing LB media and 100 $\mu$g/mL ampicillin. Transformants containing the gene encoding the instant polypeptides are then screened for the correct orientation with respect to the T7 promoter by restriction enzyme analysis.

For high level expression, a plasmid clone with the cDNA insert in the correct orientation relative to the T7 promoter can be transformed into E. coli strain BL21 (DE3) (Studier et al. (1986) J. Mol. Biol. 189:113–130). Cultures are grown in LB medium containing ampicillin (100 mg/L) at 25° C. At an optical density at 600 nm of approximately 1, IPTG (isopropylthio-$\beta$-galactoside, the inducer) can be added to a final concentration of 0.4 mM and incubation can be continued for 3 h at 25°. Cells are then harvested by centrifugation and re-suspended in 50 $\mu$L of 50 mM Tris-HCl at pH 8.0 containing 0.1 mM DTT and 0.2 mM phenyl methylsulfonyl fluoride. A small amount of 1 mm glass beads can be added and the mixture sonicated 3 times for about 5 seconds each time with a microprobe sonicator. The mixture is centrifuged and the protein concentration of the supernatant determined. One $\mu$g of protein from the soluble fraction of the culture can be separated by SDS-polyacrylamide gel electrophoresis. Gels can be observed for protein bands migrating at the expected molecular weight.

Example 7

Evaluating Compounds for Their Ability to Inhibit the Activity of a Histidine Biosynthetic Enzyme The polypeptides described herein may be produced using any number of methods known to those skilled in the art. Such methods include, but are not limited to, expression in bacteria as described in Example 6, or expression in eukaryotic cell culture, in planta, and using viral expression systems in suitably infected organisms or cell lines. The instant polypeptides may be expressed either as mature forms of the proteins as observed in vivo or as fusion proteins by covalent attachment to a variety of enzymes, proteins or affinity tags. Common fusion protein partners include glutathione S-transferase ("OGT"), thioredoxin ("Trx"), maltose binding protein, and C- and/or N-terminal hexahistidine polypeptide ("(His)$_6$"). The fusion proteins may be engineered with a protease recognition site at the fusion point so that fusion partners can be separated by protease digestion to yield intact mature enzyme. Examples of such proteases include thrombin, enterokinase and factor Xa. However, any protease can be used which specifically cleaves the peptide connecting the fusion protein and the enzyme.

Purification of the instant polypeptides, if desired, may utilize any number of separation technologies familiar to those skilled in the art of protein purification. Examples of such methods include, but are not limited to, homogenization, filtration, centrifugation, heat denaturation, ammonium sulfate precipitation, desalting, pH precipitation, ion exchange chromatography, hydrophobic interaction chromatography and affinity chromatography, wherein the affinity ligand represents a substrate, substrate analog or inhibitor. When the instant polypeptides are expressed as fusion proteins, the purification protocol may include the use of an affinity resin which is specific for the fusion protein tag attached to the expressed enzyme or an affinity resin containing ligands which are specific for the enzyme. For example, the instant polypeptides may be expressed as a fusion protein coupled to the C-terminus of thioredoxin. In addition, a (His)$_6$ peptide may be engineered into the N-terminus of the fused thioredoxin moiety to afford additional opportunities for affinity purification. Other suitable affinity resins could be synthesized by linking the appropriate ligands to any suitable resin such as Sepharose-4B. In an alternate embodiment, a thioredoxin fusion protein may be eluted using dithiothreitol; however, elution may be accomplished using other reagents which interact to displace the thioredoxin from the resin. These reagents include p-mercaptoethanol or other reduced thiol. The eluted fusion protein may be subjected to further purification by traditional means as stated above, if desired. Proteolytic cleavage of the thioredoxin fusion protein and the enzyme may be accomplished after the fusion protein is purified or while the protein is still bound to the ThioBond™ affinity resin or other resin.

Crude, partially purified or purified enzyme, either alone or as a fusion protein, may be utilized in assays for the evaluation of compounds for their ability to inhibit enzymatic activation of the instant polypeptides disclosed herein.

Example 8

Development of an Assay to Measure the Activity of a Histidine Biosynthetic Enzyme Measurement of the optimal activity of histidine biosynthetic enzymes may be accomplished by suppression of the His auxotrophy of corresponding Escherichia coli hisH and hisF mutants. An assay was developed for in vitro analysis of HisHF activity. The substrate for HisHF, PRFAR [(N$^1$-[(5'-phosphoribulosyl) formimino]-5-aminoimidazole-4-carboxamide ribonucleotide)], was synthesized by an enzymatic reaction of ATP and PRPP (phosphoribosyl pyrophosphate). The reaction is catalyzed by a mixture of the enzymes including HisA, HisG, HisI, which catalyze the first four steps in histidine biosynthesis pathway leading to the formation of PRFAR. PRFAR was purified by Q-Sepharose chromatography followed by HPLC using a $C_{18}$ column. Purified PRFAR has the expected UV spectrum with major peak at $OD_{290}$.

The HisHF catalyzed conversion of PRFAR to AICAR and IGP is monitored at $O.D._{300}$ for the decrease of PRFAR level. The optimized buffer condition was determined to be 15 mM KPi, pH 7.5, 5 mM Glutamine, 100 µM PRFAR. The steady state kinetic constants were determined for HisHF by varying the concentration of PRFAR or glutamine, the two substrates for the reaction.

Example 9

Determination of Amino Acids Essential for Histidine Biosynthetic Enzyme Activity Site-directed mutagenesis of the HisHF enzyme allows the determination of the amino acids essential for activity and catalysis. Site-directed mutagenesis was carried out for, both, the hisH domain (glutamine amidotransferase) and the hisF domain (cyclase). Based on sequence homology with other trpG-type glutamine amidotransferases and the cysteine protease family, three conserved residues in the hisH domain that constitute the putative "catalytic triad" for the glutamine amidotransfer step were mutagenized. The mutants (based on the *Arabidopsis thaliana* sequence, SEQ ID NO:15) include Cys141→Ala or Ser; His246→Ala; Glu248→Ala or Gln. All of the hisH-domain mutants were constructed by gap repair recombination and found to be unable to complement the yeast mutant strain ZXY72-1B indicating that these residues are probably essential for the function of the glutamine amidotransferase domain, consistent with their proposed role in the putative catalytic triad.

Little biochemical study has been done for the F domain of HisHF enzyme. HisF shares a low level homology to HisA enzyme, the 5'-PRFAR isomerase which catalyzes the enzymatic step before hisF. Based on the sequence homology between yeast HisHF and other HisF proteins, we identified a group of highly conserved charged residues that are likely to be important for substrate binding or catalysis for the cyclase reaction, which involves an abstraction of a proton to give the product IGP (imidazole glycerol phosphate). An alanine scanning approach was undertaken for these conserved residues, the mutant clones were studied for complementation of yeast strain ZXY72-1B. The hisF domain mutants were constructed by gap repair recombination, similar to the construction of hisH domain mutants. Mutations were Lys302→Ala, Asp334→Ala, Glu336→Ala, Asp403→Ala, Lys404→Ala, Ser409→Ala, Asp447→Ala, Glu508→Ala, Asp517→Ala, and Glu553→Ala. Of these Asp403, Lys404, Asp447, Glu508, and Asp517 are unable to complement the yeast strain ZXY72-1B suggesting that they are essential for enzyme activity.

What is claimed is:

1. An isolated polynucleotide comprising:
   (a) a nucleotide sequence encoding a polypeptide having HisHF glutamine amidotransferase activity, wherein the polypeptide has an amino acid sequence of at least 90% sequence identity, based on the Clustal method of alignment, when compared to SEQ ID NO:2, or
   (b) a full complement of the nucleotide sequence of (a).

2. The polynucleotide of claim 1 wherein the amino acid sequence of the polypeptide has at least 95% sequence identity, based on the Clustal method of alignment, when compared to SEQ ID NO:2.

3. The polynucleotide of claim 1, wherein the amino acid sequence of the polypeptide comprises SEQ ID NO:2.

4. The polynucleotide of claim 1, wherein the nucleotide sequence comprises SEQ ID NO:1.

5. A recombinant DNA construct comprising the polynucleotide of claim 1, operably linked to at least one regulatory sequence.

6. The recombinant DNA construct of claim 5, wherein the recombinant DNA construct is an expression vector.

7. A transgenic cell or a virus comprising the recombinant DNA construct of claim 5.

8. The transgenic cell of claim 7, wherein the cell is selected from the group consisting of a yeast cell, a bacterial cell, an insect cell, and a plant cell.

9. A transgenic plant comprising the polynucleotide of claim 1.

10. A method for transforming a cell comprising introducing into a cell the polynucleotide of claim 1.

11. A method for producing a transgenic plant comprising (a) transforming a plant cell with the polynucleotide of claim 1, and (b) regenerating a plant from the transformed plant cell.

12. A method for positive selection of a transformed cell comprising:
   (a) transforming a plant cell with the recombinant DNA construct of claim 5 or the expression vector of claim 6; and
   (b) growing the transformed plant cell under conditions allowing expression of the polynucleotide in an amount sufficient to complement a HisHF mutant histidine biosynthetic auxotroph to provide a positive selection means.

13. The method of claim 12, wherein the plant cell is a monocot.

14. The method of claim 13, wherein the monocot is corn.

* * * * *

UNITED STATES PATENT AND TRADEMARK OFFICE
CERTIFICATE OF CORRECTION

PATENT NO. : 6,855,867 B1
DATED : February 16, 2005
INVENTOR(S) : Allen Stephen M. et al.

Page 1 of 1

It is certified that error appears in the above-identified patent and that said Letters Patent is hereby corrected as shown below:

<u>Title page,</u>
Item [75], Inventor, please delete "Lisa L. Huang, 1423 Old Wilmington Rd., Hockessin, DE (US) 19707 and J. Antoni Rafaiski, 2028 Longcome Dr., Wilmington, DE (US) 19810" and insert -- Robert A. LaRossa and Guo-Hua Miao --

Signed and Sealed this

Twenty-eighth Day of June, 2005

JON W. DUDAS
*Director of the United States Patent and Trademark Office*

SEQUENCE LISTING

<160> NUMBER OF SEQ ID NOS: 15

<210> SEQ ID NO 1
<211> LENGTH: 1956
<212> TYPE: DNA
<213> ORGANISM: Impatiens balsamia

<400> SEQUENCE: 1

```
gcacgagaag gaactggcaa gtaccaagcc acagaatggg ttcagaattc gcgccgcctt    60
ggctggtgca ggcggagatt ctgtggtgac tttacttgat tacggtgctg gaaatgttag   120
gagtgtgagg aacgccatcc gcacacttgg atttgatatc aaagatgtgc aaaagccaga   180
ggatattcta aatgctaagc gccttatctt tcctggcgtt ggggcctttg cacctgcaat   240
ggatgttctt attcgtaaag ggctggctga agcactctgt acttacattc agaatgatcg   300
acctttcctg ggtatatgcc tgggattgca gctactcttt gagtcaagtg aagaaaatgg   360
tccaattcaa ggtcttggct tgattcctgg acgggttggg cgttttgaat catccaatgg   420
tttaagggtg ccacatattg gatggcatgc cttggatata aaggaagggt cagcaatttt   480
agatgatgtg gggaatcaac atgtgtattt tgttcactca tatcgagcca atgccgagga   540
caacaaagag tggatttcat ctacatgcag ctatggtgac gattttattg catccattca   600
gaagggaaat gttcatgcag tccaatttca tcccgagaag agtggaggtg ttggactttc   660
catattgaga agattttga atgctgattc ctttaacaac aaaagacaga agccaatgaa   720
tggaaaggct tctaaacttg caaagagagt aattgcttgc cttgatgtga gggcaaatga   780
taatggggat cttgttgtaa ccaagggaga ccaatatgat gtgagagaac gtacagaaga   840
gaatgaggtc agaaaccttg gcaagcctgt tgaacttgct gggcagtatt atttagacgg   900
```

-continued

```
tgctgatgag gtcagcttct taaacattac tggtttccgg gacttccctc taggcgatct     960
acccatgcta caggtcttgc aacgcgcatc tgaaaacgtt tttgtgccat taactgtcgg    1020
gggtggcatc agggatttta ctgatgcaaa tggaaggtat tattctagtc tagaagtggc    1080
ttcagagtat ttcagatcgg gcgccgataa ggtttcgatc ggaagtgatg cagtttacac    1140
tgctgaggaa tatattaaaa ccggagtgaa gacaggaaag agcagcatag agcagatatc    1200
tacagtatat ggtaaccagg cagtggttgt aagcattgat cctcgccgag tttacttgag    1260
aaaacccgat gaagtagaat ttaaagccat caaagtaagc catccaggtc caaacggtga    1320
ggaatatgcc tggtatcagt gcactgttaa tggtggacga gaaggagac ccatcggagc     1380
ttatgaacta gctaaggctg ttgaggaact tggagctgga gaaatattat tgaactgcat    1440
tgattgtgat ggtcaaggaa aaggattcga tatagatctg atcaagctaa tatccgatgc    1500
tgtgaacatt cctgttatcg caagcagcgg tgcaggagtc gctgatcact tctccgaagt    1560
ctttaatgaa accaacgcat ctgctgccct tgcagctggc attttccatc gcaaagaggt    1620
tccaattaag gctgttaaag agcacttgtt gaaggaaggg attgaagtta gattgtaagg    1680
cgagaatcac ttggaagaaa tttcatcttg aagttcaatt ttgttacaca agagatttcc    1740
ttctttcttg gcctatgtga tatttattta tttatgtttt gctattgaat tattgttatt    1800
attattttgg catttgttat ttgaatagat ttgagttttt agaccttggt gtgtcctgtt    1860
tatctctagg ccatgttttg tggattatat acaagtgtga aattaaataa ataaatcgta    1920
tgaatttatg cttttaaaaa aaaaaaaaa aaaaaa                                1956
```

<210> SEQ ID NO 2
<211> LENGTH: 558
<212> TYPE: PRT
<213> ORGANISM: Impatiens balsamia

<400> SEQUENCE: 2

```
His Glu Lys Glu Leu Ala Ser Thr Lys Pro Gln Asn Gly Phe Arg Ile
  1               5                  10                  15

Arg Ala Ala Leu Ala Gly Ala Gly Gly Asp Ser Val Val Thr Leu Leu
             20                  25                  30

Asp Tyr Gly Ala Gly Asn Val Arg Ser Val Arg Asn Ala Ile Arg Thr
         35                  40                  45

Leu Gly Phe Asp Ile Lys Asp Val Gln Lys Pro Glu Asp Ile Leu Asn
     50                  55                  60

Ala Lys Arg Leu Ile Phe Pro Gly Val Gly Ala Phe Ala Pro Ala Met
 65                  70                  75                  80

Asp Val Leu Ile Arg Lys Gly Leu Ala Glu Ala Leu Cys Thr Tyr Ile
                 85                  90                  95

Gln Asn Asp Arg Pro Phe Leu Gly Ile Cys Leu Gly Leu Gln Leu Leu
            100                 105                 110

Phe Glu Ser Ser Glu Glu Asn Gly Pro Ile Gln Gly Leu Gly Leu Ile
        115                 120                 125

Pro Gly Arg Val Gly Arg Phe Glu Ser Ser Asn Gly Leu Arg Val Pro
    130                 135                 140

His Ile Gly Trp His Ala Leu Asp Ile Lys Glu Gly Ser Ala Ile Leu
145                 150                 155                 160

Asp Asp Val Gly Asn Gln His Val Tyr Phe Val His Ser Tyr Arg Ala
                165                 170                 175

Asn Ala Glu Asp Asn Lys Glu Trp Ile Ser Ser Thr Cys Ser Tyr Gly
            180                 185                 190
```

```
Asp Asp Phe Ile Ala Ser Ile Gln Lys Gly Asn Val His Ala Val Gln
        195                 200                 205

Phe His Pro Glu Lys Ser Gly Val Gly Leu Ser Ile Leu Arg Arg
210                 215                 220

Phe Leu Asn Ala Asp Ser Phe Asn Asn Lys Arg Gln Lys Pro Met Asn
225                 230                 235                 240

Gly Lys Ala Ser Lys Leu Ala Lys Arg Val Ile Ala Cys Leu Asp Val
                245                 250                 255

Arg Ala Asn Asp Asn Gly Asp Leu Val Val Thr Lys Gly Asp Gln Tyr
            260                 265                 270

Asp Val Arg Glu Arg Thr Glu Glu Asn Glu Val Arg Asn Leu Gly Lys
        275                 280                 285

Pro Val Glu Leu Ala Gly Gln Tyr Tyr Leu Asp Gly Ala Asp Glu Val
    290                 295                 300

Ser Phe Leu Asn Ile Thr Gly Phe Arg Asp Phe Pro Leu Gly Asp Leu
305                 310                 315                 320

Pro Met Leu Gln Val Leu Gln Arg Ala Ser Glu Asn Val Phe Val Pro
                325                 330                 335

Leu Thr Val Gly Gly Gly Ile Arg Asp Phe Thr Asp Ala Asn Gly Arg
            340                 345                 350

Tyr Tyr Ser Ser Leu Glu Val Ala Ser Glu Tyr Phe Arg Ser Gly Ala
        355                 360                 365

Asp Lys Val Ser Ile Gly Ser Asp Ala Val Tyr Thr Ala Glu Glu Tyr
    370                 375                 380

Ile Lys Thr Gly Val Lys Thr Gly Lys Ser Ser Ile Glu Gln Ile Ser
385                 390                 395                 400

Thr Val Tyr Gly Asn Gln Ala Val Val Ser Ile Asp Pro Arg Arg
                405                 410                 415

Val Tyr Leu Arg Lys Pro Asp Glu Val Glu Phe Lys Ala Ile Lys Val
            420                 425                 430

Ser His Pro Gly Pro Asn Gly Glu Glu Tyr Ala Trp Tyr Gln Cys Thr
        435                 440                 445

Val Asn Gly Gly Arg Glu Gly Arg Pro Ile Gly Ala Tyr Glu Leu Ala
    450                 455                 460

Lys Ala Val Glu Glu Leu Gly Ala Gly Leu Ile Leu Asn Cys Ile
465                 470                 475                 480

Asp Cys Asp Gly Gln Gly Lys Gly Phe Asp Ile Asp Leu Ile Lys Leu
                485                 490                 495

Ile Ser Asp Ala Val Asn Ile Pro Val Ile Ala Ser Ser Gly Ala Gly
            500                 505                 510

Val Ala Asp His Phe Ser Glu Val Phe Asn Glu Thr Asn Ala Ser Ala
        515                 520                 525

Ala Leu Ala Ala Gly Ile Phe His Arg Lys Glu Val Pro Ile Lys Ala
    530                 535                 540

Val Lys Glu His Leu Leu Lys Glu Gly Ile Glu Val Arg Leu
545                 550                 555

<210> SEQ ID NO 3
<211> LENGTH: 587
<212> TYPE: DNA
<213> ORGANISM: Zea mays
<220> FEATURE:
<221> NAME/KEY: unsure
<222> LOCATION: (495)
<220> FEATURE:
```

```
<221> NAME/KEY: unsure
<222> LOCATION: (518)
<220> FEATURE:
<221> NAME/KEY: unsure
<222> LOCATION: (577)
<220> FEATURE:
<221> NAME/KEY: unsure
<222> LOCATION: (582)

<400> SEQUENCE: 3
aagaaaaggc cgctagggc gccgagacag cggaacgttc tctgagtttg agcacgatct      60
ccccgggccc cggcgccgcc gtacgtcccc cttcggcgtc gccagccgcc tcctggctcc    120
ggctccttca tcgcctgctc cagcgtgcct gcgtgacata agcgtcgatt gattggcgag    180
aaagggacg aatgcagccg ccgttgcagg cgcaggagc aatggctaac gtcgccgcta      240
tcctcaccgt ccctgctcc gcgggccgcc gcccgaagcg gagcaaccag ccccgcggat    300
gcggctccgt ctccgtctcc gtctccgtcc gtgcgtcctc cggcgcaaac acggtgactc    360
tgctggacta cggcgcgggg aacgtacgca gcgtgcgcaa cgcaattcgc tacctcggct    420
tcgacatccg cgacgtgcag agcccggarg acatcgtcgc cggcggaayg ggtcgtctt    480
cccggtgtcg gcgcnttcgg ctccgccatg gacgtccnca ccaggacggg catgccaacg    540
cactccgtga gtacatccaa agggaacgcc ccttccnagg cnctgcc                  587

<210> SEQ ID NO 4
<211> LENGTH: 130
<212> TYPE: PRT
<213> ORGANISM: Zea mays
<220> FEATURE:
<221> NAME/KEY: UNSURE
<222> LOCATION: (90)
<220> FEATURE:
<221> NAME/KEY: UNSURE
<222> LOCATION: (93)
<220> FEATURE:
<221> NAME/KEY: UNSURE
<222> LOCATION: (109)
<220> FEATURE:
<221> NAME/KEY: UNSURE
<222> LOCATION: (115)
<220> FEATURE:
<221> NAME/KEY: UNSURE
<222> LOCATION: (129)

<400> SEQUENCE: 4

Met Gln Pro Pro Leu Gln Ala Gln Gly Ala Met Ala Asn Val Ala Ala
 1               5                  10                  15

Ile Leu Thr Val Pro Cys Ser Ala Gly Arg Arg Pro Lys Arg Ser Asn
             20                  25                  30

Gln Pro Arg Gly Cys Gly Ser Val Ser Val Ser Val Ser Val Arg Ala
         35                  40                  45

Ser Ser Gly Ala Asn Thr Val Thr Leu Leu Asp Tyr Gly Ala Gly Asn
     50                  55                  60

Val Arg Ser Val Arg Asn Ala Ile Arg Tyr Leu Gly Phe Asp Ile Arg
 65                  70                  75                  80

Asp Val Gln Ser Pro Glu Asp Ile Val Xaa Ala Glu Xaa Val Val Phe
                 85                  90                  95

Pro Gly Val Gly Ala Phe Gly Ser Ala Met Asp Val Xaa Thr Arg Thr
            100                 105                 110

Gly Met Xaa Asn Ala Leu Arg Glu Tyr Ile Gln Arg Glu Arg Pro Phe
        115                 120                 125

Xaa Gly
```

<210> SEQ ID NO 5
<211> LENGTH: 1084
<212> TYPE: DNA
<213> ORGANISM: Zea mays

<400> SEQUENCE: 5

```
actagtggta acaaaaggcg atcaatatga tgtaagagat catactagca gcaaagaggt      60
aagaaacctt ggcaagccag tcgatttagc aagccagtac tacatagacg gtgctgatga     120
ggtcagcttc ttgaatataa ctggtttccg tgactttcca ttgggtgatt tgccaatgct     180
agaggtactg cgttgtgcct ctgaaaaggt ttttgtgcca cttacagttg gtggggggcat    240
acgagacttc acagatgcaa atggaagata ctactcaagt tggaggtag catcagaata     300
tttcaggtcc ggtgctgaca aaatttcaat tggaagtgat gctgtttatg ctgctgaagc    360
cttttttacag actggtgtaa agacagggaa aagcagcttg gagcaaatct ctagagtata    420
tggcaatcag gctgtagttg tcagtattga tcctcgacgg gtatatgtca aaagtcaaga    480
agatgtgcca tttaaaactg taaggtgtc cactaaaggt ccatcgggag aagaatatgc     540
atggtaccag tgcacagtga atggtggacg tgatagccga gctataggag catatgaact    600
agcgaaagct gtggaagaat tgggcgcagg agaaatactt cttaactgca ttgattgtga    660
tggccaaggt tgtggatttg acatagattt ggttaaaatg gtttctgatg ctgtgacaat    720
ccctgtcatt gcgagcagtg gtgctggagc tgttcaacat ttttctgaaa tttttgagaa    780
aacaaatgct tctgctgccc ttgctgctgg cattttccac cggaaagagg ttcctatact    840
agcagtgaaa gagcatctgg tcaatgctgg tgtggaggtc agggtgtaac agggagatcc    900
ttcggtttat tgaaatattc ttgtttgatg tcacaactgc tatcagttct gtttctctga    960
tgtcgcaact gctatcagat ctgttggtgg cagctggcag tgcataggcc cctgtcgaga   1020
actgcagttt ggtaataaat taataatgtg atgcttaaca gattaaaaaa aaaaaaaaaa   1080
aaaa                                                                1084
```

<210> SEQ ID NO 6
<211> LENGTH: 295
<212> TYPE: PRT
<213> ORGANISM: Zea mays

<400> SEQUENCE: 6

```
Leu Val Val Thr Lys Gly Asp Gln Tyr Asp Val Arg Asp His Thr Ser
 1               5                  10                  15

Ser Lys Glu Val Arg Asn Leu Gly Lys Pro Val Asp Leu Ala Ser Gln
            20                  25                  30

Tyr Tyr Ile Asp Gly Ala Asp Glu Val Ser Phe Leu Asn Ile Thr Gly
        35                  40                  45

Phe Arg Asp Phe Pro Leu Gly Asp Leu Pro Met Leu Glu Val Leu Arg
    50                  55                  60

Cys Ala Ser Glu Lys Val Phe Val Pro Leu Thr Val Gly Gly Gly Ile
65                  70                  75                  80

Arg Asp Phe Thr Asp Ala Asn Gly Arg Tyr Tyr Ser Ser Leu Glu Val
                85                  90                  95

Ala Ser Glu Tyr Phe Arg Ser Gly Ala Asp Lys Ile Ser Ile Gly Ser
            100                 105                 110

Asp Ala Val Tyr Ala Ala Glu Ala Phe Leu Gln Thr Gly Val Lys Thr
        115                 120                 125
```

```
Gly Lys Ser Ser Leu Glu Gln Ile Ser Arg Val Tyr Gly Asn Gln Ala
    130                 135                 140

Val Val Val Ser Ile Asp Pro Arg Arg Val Tyr Val Lys Ser Gln Glu
145                 150                 155                 160

Asp Val Pro Phe Lys Thr Val Lys Val Ser Thr Lys Gly Pro Ser Gly
                165                 170                 175

Glu Glu Tyr Ala Trp Tyr Gln Cys Thr Val Asn Gly Gly Arg Asp Ser
            180                 185                 190

Arg Ala Ile Gly Ala Tyr Glu Leu Ala Lys Ala Val Glu Glu Leu Gly
        195                 200                 205

Ala Gly Glu Ile Leu Leu Asn Cys Ile Asp Cys Asp Gly Gln Gly Cys
    210                 215                 220

Gly Phe Asp Ile Asp Leu Val Lys Met Val Ser Asp Ala Val Thr Ile
225                 230                 235                 240

Pro Val Ile Ala Ser Ser Gly Ala Gly Ala Val Gln His Phe Ser Glu
                245                 250                 255

Ile Phe Glu Lys Thr Asn Ala Ser Ala Ala Leu Ala Ala Gly Ile Phe
            260                 265                 270

His Arg Lys Glu Val Pro Ile Leu Ala Val Lys Glu His Leu Val Asn
        275                 280                 285

Ala Gly Val Glu Val Arg Val
    290                 295

<210> SEQ ID NO 7
<211> LENGTH: 494
<212> TYPE: DNA
<213> ORGANISM: Zea mays
<220> FEATURE:
<221> NAME/KEY: unsure
<222> LOCATION: (6)
<220> FEATURE:
<221> NAME/KEY: unsure
<222> LOCATION: (12)
<220> FEATURE:
<221> NAME/KEY: unsure
<222> LOCATION: (43)
<220> FEATURE:
<221> NAME/KEY: unsure
<222> LOCATION: (56)
<220> FEATURE:
<221> NAME/KEY: unsure
<222> LOCATION: (60)
<220> FEATURE:
<221> NAME/KEY: unsure
<222> LOCATION: (154)..(155)
<220> FEATURE:
<221> NAME/KEY: unsure
<222> LOCATION: (161)
<220> FEATURE:
<221> NAME/KEY: unsure
<222> LOCATION: (163)
<220> FEATURE:
<221> NAME/KEY: unsure
<222> LOCATION: (166)
<220> FEATURE:
<221> NAME/KEY: unsure
<222> LOCATION: (202)
<220> FEATURE:
<221> NAME/KEY: unsure
<222> LOCATION: (215)
<220> FEATURE:
<221> NAME/KEY: unsure
<222> LOCATION: (266)
<220> FEATURE:
<221> NAME/KEY: unsure
<222> LOCATION: (271)
<220> FEATURE:
```

<221> NAME/KEY: unsure
<222> LOCATION: (274)..(275)
<220> FEATURE:
<221> NAME/KEY: unsure
<222> LOCATION: (277)
<220> FEATURE:
<221> NAME/KEY: unsure
<222> LOCATION: (306)
<220> FEATURE:
<221> NAME/KEY: unsure
<222> LOCATION: (320)
<220> FEATURE:
<221> NAME/KEY: unsure
<222> LOCATION: (346)..(347)
<220> FEATURE:
<221> NAME/KEY: unsure
<222> LOCATION: (356)
<220> FEATURE:
<221> NAME/KEY: unsure
<222> LOCATION: (393)
<220> FEATURE:
<221> NAME/KEY: unsure
<222> LOCATION: (434)
<220> FEATURE:
<221> NAME/KEY: unsure
<222> LOCATION: (441)
<220> FEATURE:
<221> NAME/KEY: unsure
<222> LOCATION: (456)
<220> FEATURE:
<221> NAME/KEY: unsure
<222> LOCATION: (466)
<220> FEATURE:
<221> NAME/KEY: unsure
<222> LOCATION: (474)

<400> SEQUENCE: 7

| | | | | | |
|---|---|---|---|---|---|
| tcgggnccncg | gngattcccg | gggtcgagcc | aacgggtccg | gtncctcaaa | caaggncggn | 60 |
| catggtcaac | gcactccggt | ggagtatatc | caagagggac | cggccccttc | ctaggcatct | 120 |
| gcctcggtct | ccagctgctc | ttcggattcc | agcnnggaga | nanggnccgt | gtgagcggac | 180 |
| tcggtgtgat | atcaggcgtg | gncaggcgat | tcgantcctc | aaatggcctc | atagttccac | 240 |
| atgttggctg | gaacgctctc | cagatnacca | nggnnanacc | actgttgcag | ggagctgatg | 300 |
| gccagnatgt | gtacttttgn | tcactcctac | cgcgtactgg | cttcanngtg | ctagtnagga | 360 |
| aactggggt | tcctccatat | ggcaactatg | ggngacagct | tttaatcctc | catctcaaat | 420 |
| ggggcaacat | tcanggcaag | ntcaaatttc | acccangaaa | agagtnggaa | gctncccggg | 480 |
| actttcctat | tcct | | | | | 494 |

<210> SEQ ID NO 8
<211> LENGTH: 86
<212> TYPE: PRT
<213> ORGANISM: Zea mays
<220> FEATURE:
<221> NAME/KEY: UNSURE
<222> LOCATION: (23)
<220> FEATURE:
<221> NAME/KEY: UNSURE
<222> LOCATION: (25)..(26)..(27)
<220> FEATURE:
<221> NAME/KEY: UNSURE
<222> LOCATION: (39)
<220> FEATURE:
<221> NAME/KEY: UNSURE
<222> LOCATION: (43)
<220> FEATURE:
<221> NAME/KEY: UNSURE
<222> LOCATION: (60)
<220> FEATURE:
<221> NAME/KEY: UNSURE
<222> LOCATION: (62)..(63)..(64)

```
<220> FEATURE:
<221> NAME/KEY: UNSURE
<222> LOCATION: (74)
<220> FEATURE:
<221> NAME/KEY: UNSURE
<222> LOCATION: (78)

<400> SEQUENCE: 8

Tyr Pro Arg Gly Thr Gly Pro Phe Leu Gly Ile Cys Leu Gly Leu Gln
  1               5                  10                  15

Leu Leu Phe Gly Phe Gln Xaa Gly Xaa Xaa Xaa Arg Val Ser Gly Leu
             20                  25                  30

Gly Val Ile Ser Gly Val Xaa Arg Arg Phe Xaa Ser Ser Asn Gly Leu
             35                  40                  45

Ile Val Pro His Val Gly Trp Asn Ala Leu Gln Xaa Thr Xaa Xaa Xaa
 50                  55                  60

Pro Leu Leu Gln Gly Ala Asp Gly Gln Xaa Val Tyr Phe Xaa His Ser
 65                  70                  75                  80

Tyr Arg Val Leu Ala Ser
             85

<210> SEQ ID NO 9
<211> LENGTH: 495
<212> TYPE: DNA
<213> ORGANISM: Oryza sativa
<220> FEATURE:
<221> NAME/KEY: unsure
<222> LOCATION: (125)
<220> FEATURE:
<221> NAME/KEY: unsure
<222> LOCATION: (266)
<220> FEATURE:
<221> NAME/KEY: unsure
<222> LOCATION: (315)
<220> FEATURE:
<221> NAME/KEY: unsure
<222> LOCATION: (366)
<220> FEATURE:
<221> NAME/KEY: unsure
<222> LOCATION: (405)
<220> FEATURE:
<221> NAME/KEY: unsure
<222> LOCATION: (441)
<220> FEATURE:
<221> NAME/KEY: unsure
<222> LOCATION: (443)
<220> FEATURE:
<221> NAME/KEY: unsure
<222> LOCATION: (445)
<220> FEATURE:
<221> NAME/KEY: unsure
<222> LOCATION: (453)
<220> FEATURE:
<221> NAME/KEY: unsure
<222> LOCATION: (458)
<220> FEATURE:
<221> NAME/KEY: unsure
<222> LOCATION: (461)
<220> FEATURE:
<221> NAME/KEY: unsure
<222> LOCATION: (475)
<220> FEATURE:
<221> NAME/KEY: unsure
<222> LOCATION: (480)
<220> FEATURE:
<221> NAME/KEY: unsure
<222> LOCATION: (492)
<220> FEATURE:
<221> NAME/KEY: unsure
<222> LOCATION: (494)

<400> SEQUENCE: 9
```

-continued

```
gacacacacc cccatactg ccacaagggc cgccgccgcc gccgggagcg atggtcgccg      60
ccacctccat caacgccgtc ccctgctccg ctggtcggcc gaagcggagg agccagcgcc    120
gcggngcctc tacggtcgcc gtgcgcgcgt ccggcgacgc tagcaccgtg acgctgctgg    180
actacggcgc gggcaacgtg cgcagcgtgc gcaatgccat ccgccacctc ggtttcggca    240
tccgcgacgt gcgcagcccg gagganatcc tcgccgccga ccgcctcgtc ttcccggggg    300
tcggcgcctt cgggntcaag ccatggacgt cctcaacccg ctccgggatg ggcggacgcg    360
cttccncgga gtacatccgg caggggaccc ccccttcct cgggnatctg gccttcgggg     420
cttccaagct tctccttccg nantnctaag ggnaaggnag naattggccc cggtnaggcn    480
gggcttgggg tntnt                                                     495
```

<210> SEQ ID NO 10
<211> LENGTH: 87
<212> TYPE: PRT
<213> ORGANISM: Oryza sativa
<220> FEATURE:
<221> NAME/KEY: UNSURE
<222> LOCATION: (72)

<400> SEQUENCE: 10

```
Met Val Ala Ala Thr Ser Ile Asn Ala Val Pro Cys Ser Ala Gly Arg
 1               5                  10                  15

Pro Lys Arg Arg Ser Gln Arg Gly Ala Ser Thr Val Ala Val Arg
             20                  25                  30

Ala Ser Gly Asp Ala Ser Thr Val Thr Leu Leu Asp Tyr Gly Ala Gly
         35                  40                  45

Asn Val Arg Ser Val Arg Asn Ala Ile Arg His Leu Gly Phe Gly Ile
     50                  55                  60

Arg Asp Val Arg Ser Pro Glu Xaa Ile Leu Ala Ala Asp Arg Leu Val
 65                  70                  75                  80

Phe Pro Gly Val Gly Ala Phe
                 85
```

<210> SEQ ID NO 11
<211> LENGTH: 178
<212> TYPE: DNA
<213> ORGANISM: Glycine max

<400> SEQUENCE: 11

```
ttgtgacttt gcttgattac ggtgctggca atgttcggag tgtcaggaat gcaatcagat      60
tcctcgggtt tgacataaaa gatgtgcaaa ctccgcaaga tattctgaat gcaagtcggt    120 tagttttttcc tggtgttgga gcatttgctg ctgccatgga ggtgttaagc aaaactgg      178
```

<210> SEQ ID NO 12
<211> LENGTH: 58
<212> TYPE: PRT
<213> ORGANISM: Glycine max

<400> SEQUENCE: 12

```
Val Thr Leu Leu Asp Tyr Gly Ala Gly Asn Val Arg Ser Val Arg Asn
 1               5                  10                  15

Ala Ile Arg Phe Leu Gly Phe Asp Ile Lys Asp Val Gln Thr Pro Gln
             20                  25                  30

Asp Ile Leu Asn Ala Ser Arg Leu Val Phe Pro Gly Val Gly Ala Phe
         35                  40                  45
```

```
Ala Ala Ala Met Glu Val Leu Ser Lys Thr
    50                  55

<210> SEQ ID NO 13
<211> LENGTH: 671
<212> TYPE: DNA
<213> ORGANISM: Glycine max
<220> FEATURE:
<221> NAME/KEY: unsure
<222> LOCATION: (276)

<400> SEQUENCE: 13
gtatgtaaag gatcctaatg atgtgcaatt gaagaccata agggtttcaa gtccaggttc      60
aaatggagag gaatatgcat ggtatcaatg tacagttaat gggggacgag agggccggcc     120
aattggtgct tatgaactag caaaagcagt tgaagagctt ggtgctggtg aaatactact     180
taattgcatt gattgcgacg gtcaagggaa aggatttgat gtagatttaa ttaagttgat     240
atcaaatgct gtaagtatcc ctgttatcgc aagtancggt gctggtgctc ctgaacactt     300
ctctgaggtg ttctataaaa caaatgcatc agcagcactt gctgctggca ttttcacag      360 gaaagaggtg cctattcagt cggtaaaaga gcatttgttg aaggaaggca tagaagttcg     420
aatctgatca tatgcattta gtggtaaaat ttttgagatg cacttcataa taatcaaacc     480
ttgtacgtta tccctttttg tgtaatctaa cgaagctctc aaaatgtcaa ccttttggat     540
catgaaaaga ttttcacaac gagacctttc ctttgtaata ttttaagga aaatatattt      600 accatgtgca gcactatctc tgaacatttg ttattacaaa attatttcat gtgtcaaaaa     660
aaaaaaaaaa a                                                         671

<210> SEQ ID NO 14
<211> LENGTH: 141
<212> TYPE: PRT
<213> ORGANISM: Glycine max
<220> FEATURE:
<221> NAME/KEY: UNSURE
<222> LOCATION: (92)

<400> SEQUENCE: 14

Tyr Val Lys Asp Pro Asn Asp Val Gln Leu Lys Thr Ile Arg Val Ser
 1               5                  10                  15

Ser Pro Gly Ser Asn Gly Glu Glu Tyr Ala Trp Tyr Gln Cys Thr Val
            20                  25                  30

Asn Gly Gly Arg Glu Gly Arg Pro Ile Gly Ala Tyr Glu Leu Ala Lys
        35                  40                  45

Ala Val Glu Glu Leu Gly Ala Gly Glu Ile Leu Leu Asn Cys Ile Asp
    50                  55                  60

Cys Asp Gly Gln Gly Lys Gly Phe Asp Val Asp Leu Ile Lys Leu Ile
65                  70                  75                  80

Ser Asn Ala Val Ser Ile Pro Val Ile Ala Ser Xaa Gly Ala Gly Ala
                85                  90                  95

Pro Glu His Phe Ser Glu Val Phe Tyr Lys Thr Asn Ala Ser Ala Ala
            100                 105                 110

Leu Ala Ala Gly Ile Phe His Arg Lys Glu Val Pro Ile Gln Ser Val
        115                 120                 125

Lys Glu His Leu Leu Lys Glu Gly Ile Glu Val Arg Ile
    130                 135                 140

<210> SEQ ID NO 15
<211> LENGTH: 593
```

-continued

```
<212> TYPE: PRT
<213> ORGANISM: Arabidopsis thaliana

<400> SEQUENCE: 15

Met Glu Ala Thr Ala Ala Pro Phe Ser Ser Ile Val Ser Ser Arg Gln
 1               5                  10                  15

Asn Phe Ser Ser Ser Ser Ile Arg Ala Ser Ser Pro Ala Ser Leu
            20                  25                  30

Phe Leu Ser Gln Lys Ser Ile Gly Asn Val Asn Arg Lys Phe Lys Ser
            35                  40                  45

Pro Arg Ser Leu Ser Val Arg Ala Ser Ser Thr Ser Asp Ser Val Val
 50                  55                  60

Thr Leu Leu Asp Tyr Gly Ala Gly Asn Val Arg Ser Ile Arg Asn Ala
 65                  70                  75                  80

Leu Arg His Leu Gly Phe Ser Ile Lys Asp Val Gln Thr Pro Gly Asp
                    85                  90                  95

Ile Leu Asn Ala Asp Arg Leu Ile Phe Pro Val Gly Pro Phe Ala
                100                 105                 110

Pro Ala Met Asp Val Leu Asn Arg Thr Gly Met Ala Glu Ala Leu Cys
                115                 120                 125

Lys Tyr Ile Glu Asn Asp Arg Pro Phe Leu Gly Ile Cys Leu Gly Leu
            130                 135                 140

Gln Leu Leu Phe Asp Ser Ser Glu Gln Asn Gly Pro Val Lys Gly Leu
145                 150                 155                 160

Gly Val Ile Pro Gly Ile Val Gly Arg Phe Asp Ala Ser Ala Gly Ile
                165                 170                 175

Arg Val Pro His Ile Gly Trp Asn Ala Leu Gln Val Gly Lys Asp Ser
                180                 185                 190

Glu Ile Leu Asp Asp Val Gly Asn Arg His Val Tyr Phe Val His Ser
            195                 200                 205

Tyr Arg Ala Ile Pro Ser Asp Glu Asn Lys Asp Trp Ile Ser Ser Thr
210                 215                 220

Cys Asn Tyr Gly Glu Ser Phe Ile Ser Ser Ile Arg Arg Gly Asn Val
225                 230                 235                 240

His Ala Val Gln Phe His Pro Glu Lys Ser Gly Glu Val Gly Leu Ser
                245                 250                 255

Val Leu Arg Arg Phe Leu His Pro Lys Leu Pro Ala Thr Gln Lys Pro
                260                 265                 270

Met Glu Gly Lys Ala Ser Lys Leu Ala Lys Arg Val Ile Ala Cys Leu
            275                 280                 285

Asp Val Arg Thr Asn Asp Lys Gly Asp Leu Val Val Thr Lys Gly Asp
290                 295                 300

Gln Tyr Asp Val Arg Glu Gln Ser Asn Glu Asn Glu Val Arg Asn Leu
305                 310                 315                 320

Gly Lys Pro Val Asp Leu Ala Gly Gln Tyr Tyr Lys Asp Gly Ala Asp
                325                 330                 335

Glu Ile Ser Phe Leu Asn Ile Thr Gly Phe Arg Asp Phe Pro Leu Gly
            340                 345                 350

Asp Leu Pro Met Ile Gln Val Leu Arg Gln Thr Ser Lys Asn Val Phe
            355                 360                 365

Val Pro Leu Thr Val Gly Gly Ile Arg Asp Phe Thr Asp Ala Ser
            370                 375                 380

Gly Arg Tyr Tyr Ser Ser Leu Glu Val Ala Ala Glu Tyr Phe Arg Ser
385                 390                 395                 400
```

```
Gly Ala Asp Lys Met Ser Ile Gly Ser Asp Ala Val Phe Ala Ala Glu
                405             410                 415

Glu Phe Ile Lys Ser Gly Val Lys Thr Gly Lys Ser Ser Leu Glu Gln
            420             425             430

Ile Ser Arg Val Tyr Gly Asn Gln Ala Val Val Ser Ile Asp Pro
        435             440             445

Arg Arg Val Tyr Val Asn His Pro Asp Val Pro Tyr Lys Val Ile
    450             455             460

Arg Val Thr Asn Pro Gly Pro Asn Gly Glu Glu Tyr Ala Trp Tyr Gln
465             470             475                 480

Cys Thr Val Ser Gly Gly Gln Glu Gly Arg Pro Ile Gly Ala Phe Glu
                485             490             495

Leu Ala Lys Ala Val Glu Glu Leu Gly Ala Gly Glu Ile Leu Leu Asn
                500             505             510

Cys Ile Asn Cys Asp Gly Gln Gly Lys Gly Phe Asp Ile Asp Leu Val
            515             520             525

Lys Leu Ile Ser Asp Ser Val Gly Ile Pro Val Ile Ala Ser Ser Gly
    530             535             540

Ala Gly Thr Pro Asp His Phe Ser Glu Val Phe Glu Glu Asp Lys Arg
545             550             555             560

Ile Cys Arg Ala Cys Cys Arg His Phe Pro Pro Glu Arg Gly Tyr Gln
            565             570             575

Ser Gln Ser Val Lys Glu His Leu Gln Glu Glu Arg Ile Glu Val Arg
            580             585             590

Ile
```